US011529109B2

(12) United States Patent
Feain et al.

(10) Patent No.: US 11,529,109 B2
(45) Date of Patent: Dec. 20, 2022

(54) PATIENT POSITIONING APPARATUS

(71) Applicant: Leo Cancer Care, Inc., Middleton, WI (US)

(72) Inventors: Ilana Feain, New South Wales (AU); Stephen Towe, East Sussex (GB); Mark Strangeman, West Sussex (GB)

(73) Assignee: Leo Cancer Care, Inc., Middleton, WI (US)

(*) Notice: Subject to any disclaimer, the term of this patent is extended or adjusted under 35 U.S.C. 154(b) by 122 days.

(21) Appl. No.: 16/649,337

(22) PCT Filed: Sep. 14, 2018

(86) PCT No.: PCT/AU2018/051008
§ 371 (c)(1),
(2) Date: Mar. 20, 2020

(87) PCT Pub. No.: WO2019/056055
PCT Pub. Date: Mar. 28, 2019

(65) Prior Publication Data
US 2020/0268327 A1 Aug. 27, 2020

(30) Foreign Application Priority Data
Sep. 21, 2017 (AU) .................... 2017903847

(51) Int. Cl.
*A61B 6/04* (2006.01)
*A61B 5/00* (2006.01)
(Continued)

(52) U.S. Cl.
CPC ............ *A61B 6/0478* (2013.01); *A61B 5/055* (2013.01); *A61B 5/702* (2013.01); *A61B 6/032* (2013.01);
(Continued)

(58) Field of Classification Search
CPC ..... A61B 2562/18; A61B 5/055; A61B 5/702; A61B 6/032; A61B 6/04; A61B 6/0478;
(Continued)

(56) References Cited

U.S. PATENT DOCUMENTS 6,775,867 B1 8/2004 Kuphal et al.
7,392,554 B1 7/2008 Su et al.
(Continued)

FOREIGN PATENT DOCUMENTS

| EP | 1632182 A1 | 3/2006 |
| JP | 2000116635 A | 4/2000 |
| JP | 2011224162 A | 11/2011 |
| WO | WO 2008142695 A1 | 11/2008 |
| WO | WO 2019/056055 | 3/2019 |

OTHER PUBLICATIONS

Extended EP Search Report issued in corresponding application No. 18859167.1, dated May 18, 2021, 6 pages.
(Continued)

*Primary Examiner* — Mark D Remaly
(74) *Attorney, Agent, or Firm* — Casimir Jones S.C.; Thomas A. Isenbarger

(57) ABSTRACT

Disclosed is a patient positioning assembly for orientating a patient with respect to a radiation source. The patient positioning assembly includes a translatable member movable in a vertical direction between a vertically downwards first position and a vertically upwards second position. The patient positioning assembly further includes a patient support assembly mounted to the translatable member and adapted to rotate relative to the translatable member about a vertical axis. The patient support assembly is configurable between a first orientation, which sustains the patient in a seated position, and a second orientation, which sustains the patient in a generally standing position.

21 Claims, 37 Drawing Sheets

(51) Int. Cl.
  *A61B 6/03*    (2006.01)
  *A61B 6/10*    (2006.01)
  *A61N 5/10*    (2006.01)
  *A61B 5/055*   (2006.01)

(52) U.S. Cl.
  CPC ............ *A61B 6/0487* (2020.08); *A61B 6/107* (2013.01); *A61N 5/1045* (2013.01); *A61N 5/1077* (2013.01); *A61B 2562/18* (2013.01); *A61N 2005/1094* (2013.01); *A61N 2005/1097* (2013.01)

(58) Field of Classification Search
  CPC ............... A61B 6/0487; A61B 6/107; A61N 2005/1094; A61N 2005/1097; A61N 5/1045; A61N 5/1049; A61N 5/1069; A61N 5/1077
  See application file for complete search history.

(56) References Cited

U.S. PATENT DOCUMENTS

| | | |
|---|---|---|
| 2004/0138553 A1 | 7/2004 | Damadian |
| 2007/0189461 A1 | 8/2007 | Sommer |
| 2007/0238949 A1 | 10/2007 | Wang et al. |
| 2009/0003532 A1 | 1/2009 | Weber |
| 2012/0209109 A1 | 8/2012 | Vladimir |
| 2012/0245454 A1 | 9/2012 | Trequattrini et al. |
| 2013/0064344 A1 | 3/2013 | Carol |
| 2013/0101088 A1 | 4/2013 | Fabrizio |
| 2016/0151025 A1 | 6/2016 | Gatayama et al. |

OTHER PUBLICATIONS

International Search Report and Written Opinion issued in corresponding International application No. PCT/AU2018/051008, dated Nov. 13, 2018, 11 pages.

FIGURE 7A  FIGURE 7B

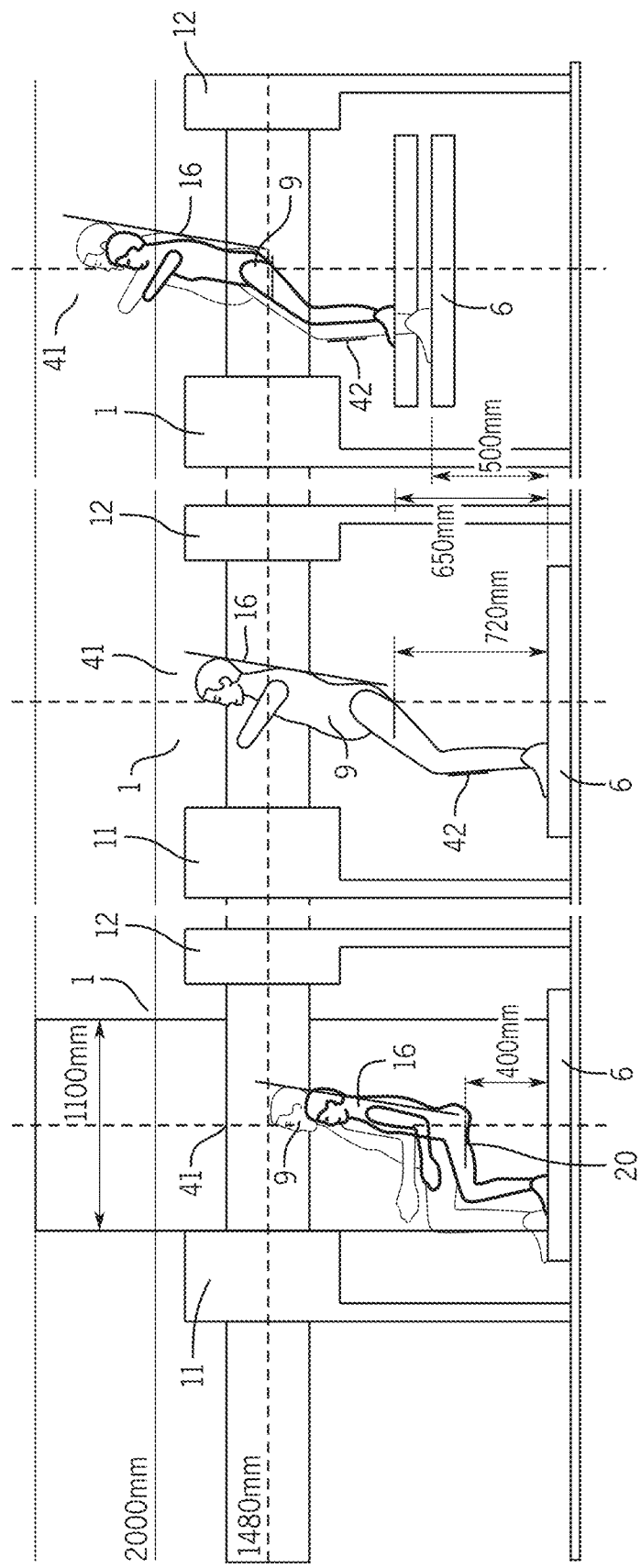

PATIENT POSITIONING APPARATUS

CROSS REFERENCE TO RELATED APPLICATIONS

This application is a § 371 national phase application of Int'l Pat. App. No. PCT/AU2018/051008, filed Sep. 14, 2018, which claims priority to Australia Application No. 2017903847, filed Sep. 21, 2017, each of which is incorporated herein by reference in its entirety.

TECHNICAL FIELD

The present invention generally relates to an apparatus for positioning a patient with respect to a radiation source such as a therapeutic treatment beam or a medical imaging beam and in particular relates to an apparatus for positioning a patient in a generally upright position.

BACKGROUND

Radiation sources have many uses in medicine, including medical imaging and radiation therapy. Generally, such radiation sources are configured to move in relation to a stationary patient lying in a supine position in order for the radiation source to target the correct part of the patient. Such arrangements are generally expensive to install and maintain, and may involve complexity in providing stability and shielding for the moving radiation source. The expense and complexity of these arrangements may limit the availability of treatment for patients from regional areas or from developing nations.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

BRIEF SUMMARY

The present invention seeks to provide an invention with improved features and properties.

In an aspect the present invention provides a patient positioning assembly for orientating a patient with respect to a radiation source, wherein the patient positioning assembly includes: a translatable member movable in a vertical direction between a vertically downwards first position and a vertically upwards second position; and a patient support assembly mounted to the translatable member and adapted to rotate relative to the translatable member about a vertical axis; wherein the patient support assembly is configurable between a first orientation, which sustains the patient in a seated position, and a second orientation, which sustains the patient in a generally standing position.

Preferably the translatable member is wholly or partially locatable in a recess in a surface supporting the patient positioning assembly when the patient positioning system is in the first position.

Preferably, in the second orientation, the patient support assembly sustains the patient in a generally standing position such that knees of the patient are bent at an angle relative to thighs of the patient and hips of the patient are bent at an angle relative to the torso of the patient.

Preferably the angle between the hips and the torso is between about 135° to about 165°.

Preferably the patient support assembly includes a back rest for sustaining a back of the patient at an angle relative to the vertical axis.

Preferably the back rest is angled posteriorly to the vertical axis at an angle between about 0° to about 20°.

Preferably the patient support assembly is moveably mounted to the translatable member and is adapted to move in a vertical direction independently of the vertical movement of the translatable member.

Preferably the patient support assembly includes a seat member, and wherein, in the first orientation, the seat member is positioned against buttocks of the patient for sustaining the patient in the seated position.

Preferably the seat member is adjustable in orientation such that, in the second orientation, the seat member is located away from the patient.

Preferably the patient support assembly includes arm rests for stabilising the patient during rotation of the patient support assembly.

Preferably the arm rests are adapted for mounting of measurement instruments thereto.

Preferably the patient support assembly includes a shin rest adjustable in position, and wherein, in the second orientation, the shin rest is positioned against shins of the patient for sustaining the patient in the generally standing position.

Preferably the patient support assembly includes foot braces for securing feet of the patient.

Preferably the patient positioning assembly further includes a base supporting the patient support assembly, the base being pivotally mounted to the translatable member such that the patient support assembly may be tilted about a point of the base.

Preferably the patient support assembly is adapted to move in a horizontal plane.

Preferably the radiation source is a therapeutic radiation source.

Preferably the radiation source is a particle or photon beam.

Preferably the therapeutic radiation source is a linear accelerator (linac) shaped by a multi-leaf collimator.

Preferably the radiation source is a medical imaging radiation source.

Preferably the medical imaging source is an MRI scanner, a positron emission tomography scanner, an ultrasound scanner, or a computed tomography scanner.

In another aspect the present invention provides a system for radiation treatment or radiation imaging of a patient including: a patient positioning assembly according to the preceding aspect; a wall defining a space in which the patient positioning assembly is located, the wall being adapted to intersect a path of a radiation beam outputted by the radiation source; a beam-stopper shield located on an opposite side of the wall relative to the patient positioning assembly; wherein the beam-stopper shield has an absorption area for absorbing the radiation beam, and wherein the absorption area has a size that is approximately equivalent to a maximum range of scattering of the radiation beam.

Preferably the beam-stopper shield includes multiple absorption layers for absorbing the radiation beam, the absorption layers being stacked over one another.

Preferably a first absorption layer has a first size and a second absorption layer has a second size that is smaller than the first size, and wherein the first and second absorption layers are stacked such that the second absorption layer is nearer to the radiation source relative to the first absorption layer.

In another aspect the present invention provides a patient support assembly configurable between a first orientation, which sustains a patient in a seated position, and a second orientation, which sustains the patient in a generally standing position.

Preferably, in the second orientation, the patient support assembly sustains the patient in a generally standing position such that knees of the patient are bent at an angle relative to thighs of the patient and hips of the patient are bent at an angle relative to the torso of the patient.

Preferably the angle between the hips and the torso is between about 135° to about 165°.

Preferably the patient support assembly includes a back rest for sustaining a back of the patient at an angle relative to a vertical axis.

Preferably the back rest is angled posteriorly to the vertical axis at an angle between about 0° to about 20°.

Preferably the patient support assembly includes a mechanism for moving the patient support assembly in a vertical direction.

Preferably the patient support assembly includes a seat member, and wherein, in the first orientation, the seat member is positioned against buttocks of the patient for sustaining the patient in the seated position.

Preferably the seat member is adjustable in orientation such that, in the second orientation, the seat member is located away from the patient.

Preferably the patient support assembly includes arm rests for sustaining arms of the patient in a predetermined position.

Preferably the arm rests are adapted for mounting of measurement instruments thereto.

Preferably the patient support assembly includes a shin rest adjustable in position, and wherein, in the second orientation, the shin rest is positioned against shins of the patient for sustaining the patient in the generally standing position.

Preferably the patient support assembly includes foot braces for securing feet of the patient in both of the first and second orientations.

Preferably the patient support assembly includes a base supporting the patient support assembly, the base being pivotable about a pivot point located in an area defined by the base.

In another aspect the present invention provides a patient positioning assembly for orientating a patient with respect to a radiation source, wherein the patient positioning assembly includes: a translatable member moveable in a vertical direction between a vertically downwards direction and a vertically upwards direction; and a patient support assembly according to the preceding aspect mounted to the translatable member and adapted to rotate relative to the translatable member about a vertical axis.

BRIEF DESCRIPTION OF FIGURES

Example embodiments should become apparent from the following description, which is given by way of example only, of at least one preferred but non-limiting embodiment, described in connection with the accompanying figures.

FIG. 28a illustrates a schematic view of an embodiment of a patient positioning assembly in a first orientation with a translatable member in a vertically downwards position;

FIG. 28b illustrates a schematic view of an embodiment of a patient positioning assembly in a second orientation with a translatable member in a vertically downwards position;

FIG. 28c illustrates a schematic view of an embodiment of a patient positioning assembly in a second orientation with a translatable member in a vertically upwards position;

FIG. 39 illustrates a side view of the patient support assembly of FIG. 37, in a second orientation, with a back rest inclined anteriorly relative to a vertical axis;

Figure 1:
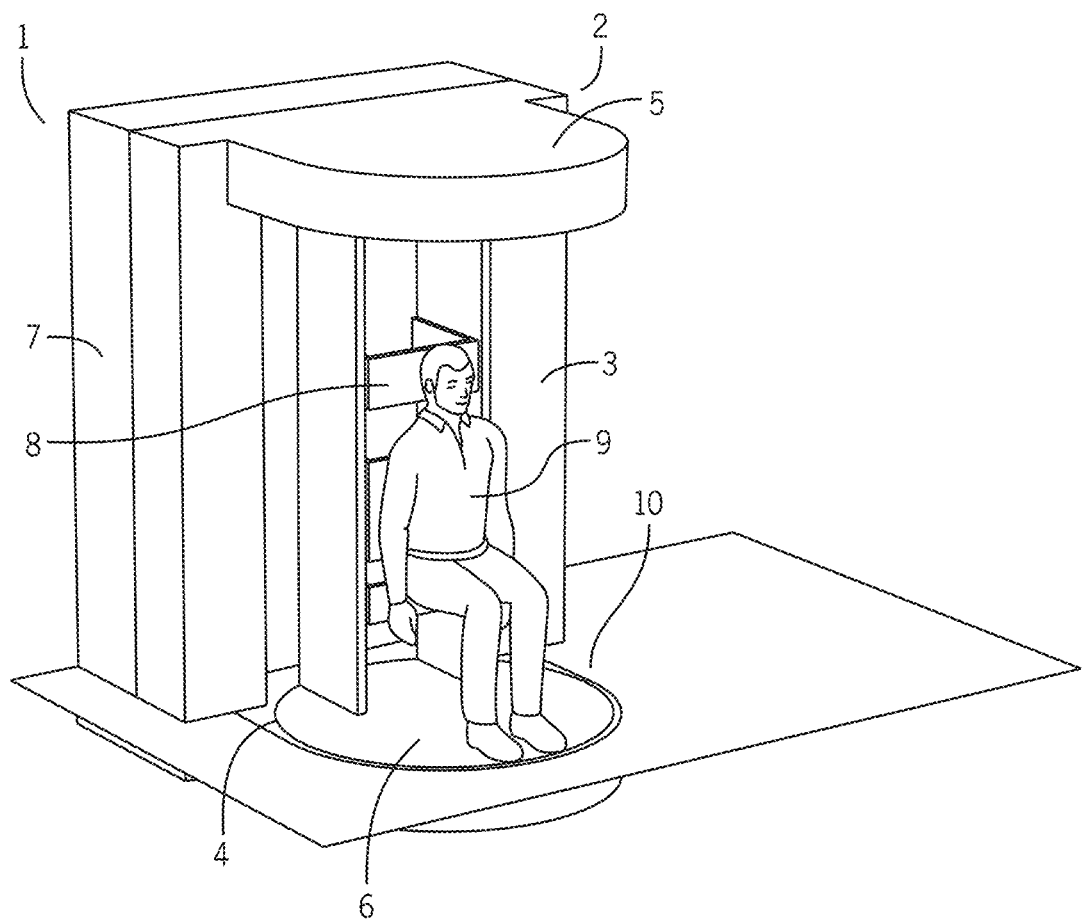
FIG. 1 illustrates an embodiment of a patient positioning assembly according to the present invention with a patient in a seated position.

PARTS LIST 1 patient positioning assembly
2 translatable member
3 main body portion of translatable member
4 first projection of translatable member
5 second projection of translatable member
6 rotating disc
7 supporting structure
8 patient support
9 patient
10 surface
11 fixed treatment beam source
12 detection panel
13 additional detection panel
14 recessed portion
15 patient restraint system
16 back rest
17 head rest
18 arm rest
20 seat member
32 elongate strap
34 shield
35 imaging beam source
36 imaging system/CT scanner
41 patient support assembly
42 shin rest
43 head restraint band
44 head restraint mould
45 first pair of rails
46 second pair of rails
47 wall
48 beam-stopper shield
49 absorption area
50 absorption layer
51 column
52 plate
53 pillar
54 platform
55 hole
56 foot brace
58 bent portion of arm rest
59 arm of arm rest
60 scissor-lift mechanism
61 fixed end of scissor-lift mechanism
62 moveable end of scissor-lift mechanism
63 pivotable base
64 spherical joint 65 stand of pivotable base
66 front actuator of pivotable base
67 rear actuator of pivotable base

PREFERRED EMBODIMENTS

The following modes, given by way of example only, are described in order to provide a more precise understanding of the subject matter of a preferred embodiment or embodiments.

In the Figures, incorporated to illustrate features of an example embodiment, like reference numerals are used to identify like parts throughout the figures.

Referring to FIG. 1, shown is an embodiment of a patient positioning assembly 1 according to the present invention. The patient positioning assembly 1 is configured to adjust the position of a patient 9 with respect to a radiation source, for example a radiation source for generating a treatment beam or an imaging beam, wherein the patient 9 is orientated in a generally upright position with a torso aligned in a vertical direction. The radiation source may be in a fixed, or stationary position. Alternatively, the radiation source may be movably mounted to change the orientation of the radiation source.

The patient positioning assembly 1 may include a translatable member 2 that may be vertically translatable such that the translatable member 2 may articulate towards and away from a surface 10 on which the patient positioning assembly 1 is supported. The translatable member 2 may be in the form of a carriage that may be orientated in a vertical direction, and include a main body portion 3. The translatable member 2 may have a first projection 4 and a second projection 5, each of which may extend from the same side of the main body portion 3 and may be displaced from each other in the vertical direction. In the embodiment of FIG. 1, the first projection 4 is located at a lower periphery of the main body portion 3, and the second projection 5 is located at an upper periphery of the main body portion 3. The main body portion 3 may have a cutaway portion, or may be formed of elongate members with space therebetween extending between the first projection 4 and the second projection 5.

The translatable member 2 may be mounted to a supporting structure 7 that is in turn mounted to the surface 10. The supporting structure 7 may provide stability to the patient positioning assembly 1 and may house the drive mechanism to affect the vertical movement of the translatable member 2.

The patient positioning assembly 1 may further include a patient support 8 that may take the form of a generally elongate structure extending between the first projection 4 and the second projection 5 in a vertical orientation. The patient support 8 may be configured to receive and secure a patient 9 in a generally upright position. The patient support 8 may be rotatably mounted to the translatable member 2 between the first projection 4 and the second projection 5 such that the patient support 8 may be rotatable about a vertical axis relative to the translatable member 2. A lower end of the patient support 8 may be mounted to a rotating disc 6 which is in turn mounted to the first projection 4 and an upper end of the patient support 8 may be mounted to another rotating disc 6 which is in turn mounted to the second projection 5. By this arrangement, the patient support 8 may be rotatably mounted to the translatable member 2 such that the patient support 8 is rotatable about a vertical axis extending between the first projection 4 and the second projection 5. Also, as the translatable member 2 is able to articulate vertically, the patient support 8 mounted to the translatable member 2 may similarly articulate vertically.

The patient support 8 may be adapted to receive a patient 9 requiring exposure to a treatment beam or to an imaging beam. The patient support 8 may be offset from the vertical axis of rotation such that the torso of a patient 9 secured to the patient support 8 may be aligned with the vertical axis of rotation. A patient 9 thus supported by the patient support 8 may have their position adjusted by the rotational coupling of the patient support 8 to the translatable member 2 and the vertical translation of the translatable member 2. By this arrangement, a patient 9 may have their position adjusted with respect to a treatment beam or an imaging beam so that the treatment beam may target the area of the patient 9 requiring treatment or imaging.

Figure 2:
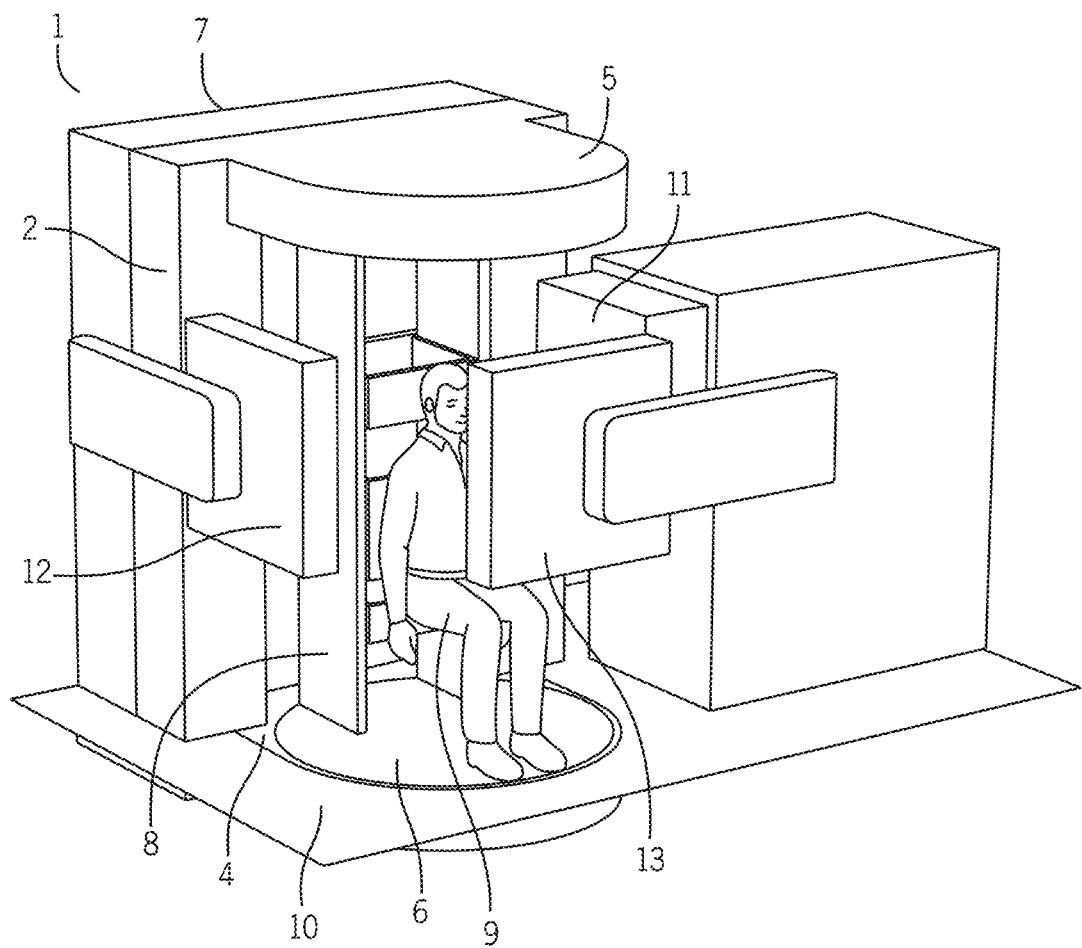
FIG. 2 illustrates the embodiment of FIG. 1 with a fixed treatment beam source and detection panels.

With reference to FIG. 2, shown is a patient 9 supported by the patient support 8 of a patient positioning assembly 1. In the depicted embodiment, the patient 9 is in a sitting position with the patient's 9 torso in a vertical upright position centered about the vertical axis of rotation. Also shown in FIG. 2 is a fixed treatment beam source 11 that is supported by the same surface 10 as the supporting structure 7 and is thus fixed in position. The treatment beam source 11 is configured to direct a fixed treatment beam towards a patient 9 positioned on the patient support 8. The treatment beam source 11 may be in the form of a liniac shaped by a multi-leaf collimator, and may be positioned to direct a beam along a horizontal direction. A detection panel 12 may be mounted to the supporting structure 7 such that the detection panel 12 is locatable in the path of the treatment beam. The detection panel 12 may be adjustably mounted so that the position of the detection panel 12 may be altered to facilitate patient 9 access to the patient support 8 for ingress and egress to the patient positioning assembly 1. The adjustable mounting may be a pivotable mounting so that the detection panel 12 may be swung away from its position in alignment with the treatment beam. An additional detection panel 13 may be mounted to the housing of the treatment beam source 11 for use in conjunction with an imaging beam source 35 (not shown), which for example may be mounted to the supporting structure 7. The additional detection panel 13 may also be adjustably mounted so that it can be moved to facilitate patient 9 access to the patient support 8. In the depicted embodiment, the imaging beam source 35 may be positioned in a horizontally orthogonal orientation to the treatment beam source 11 such that the beam paths intersect at the region of a patient 9 located on the patient support 8, though other orientations of the imaging beam source 35 are permissible. Both the treatment beam and the imaging beam may be orientated so as to intersect with the vertical axis of rotation.

FIG. 2 shows the translatable member 2 in a vertically downwards position termed the first position. The first position may locate the translatable member 2 and the patient support 8 mounted thereto near to the surface 10 supporting the patient positioning assembly 1. Accordingly, the first position may allow for patient 9 ingress to the patient positioning assembly 1 such that the patient 9 can be secured to the patient support 8. In the depicted embodiment, when the translatable member 2 is in the first position it is partially recessed into the surface 10 so that the rotating disc 6 is substantially level with the surface 10, thus facilitating patient 9 access to the patient support 8 without having to negotiate uneven surfaces. The first position may be configured so that the fixed treatment beam is directed towards the head of a patient 9 with a height of about 1900 mm when that patient 9 is secured to the patient support 8 in a seated position. This height corresponds to that of an American male patient 9 of the 95$^{th}$ height percentile, making the patient positioning assembly 1 adaptable for used with a large portion of the population, though other arrangements are equally permissible.

Figure 3:
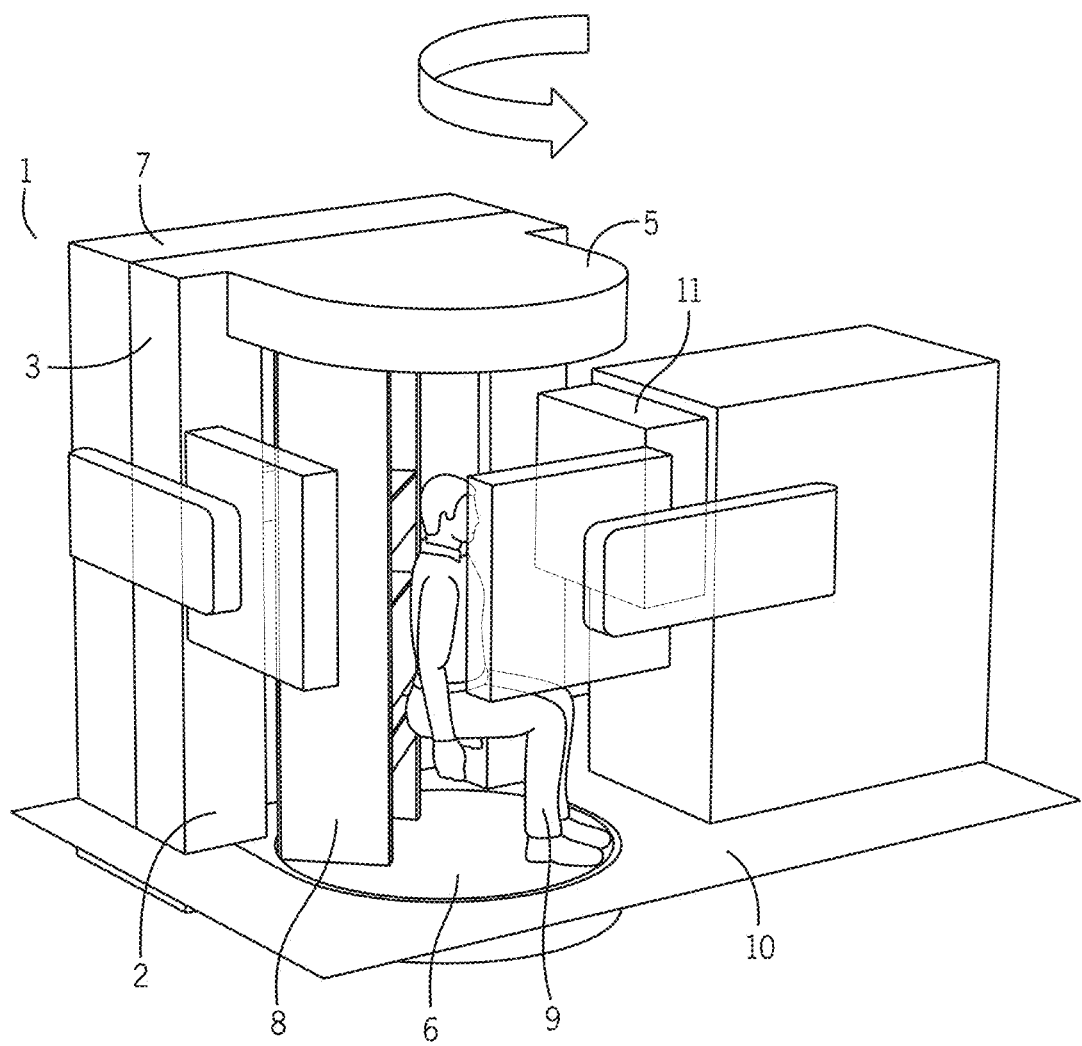
FIG. 3 illustrates the embodiment of FIG. 2 with the patient's position rotated.

FIG. 3 shows the same embodiment of the patient positioning assembly 1 as FIG. 2, with the translatable member 2 in the first position, but with the patient support 8 rotated about the vertical axis so that the fixed treatment beam is able to target a different part of the patient's 9 head to FIG. 2.

Figure 4:
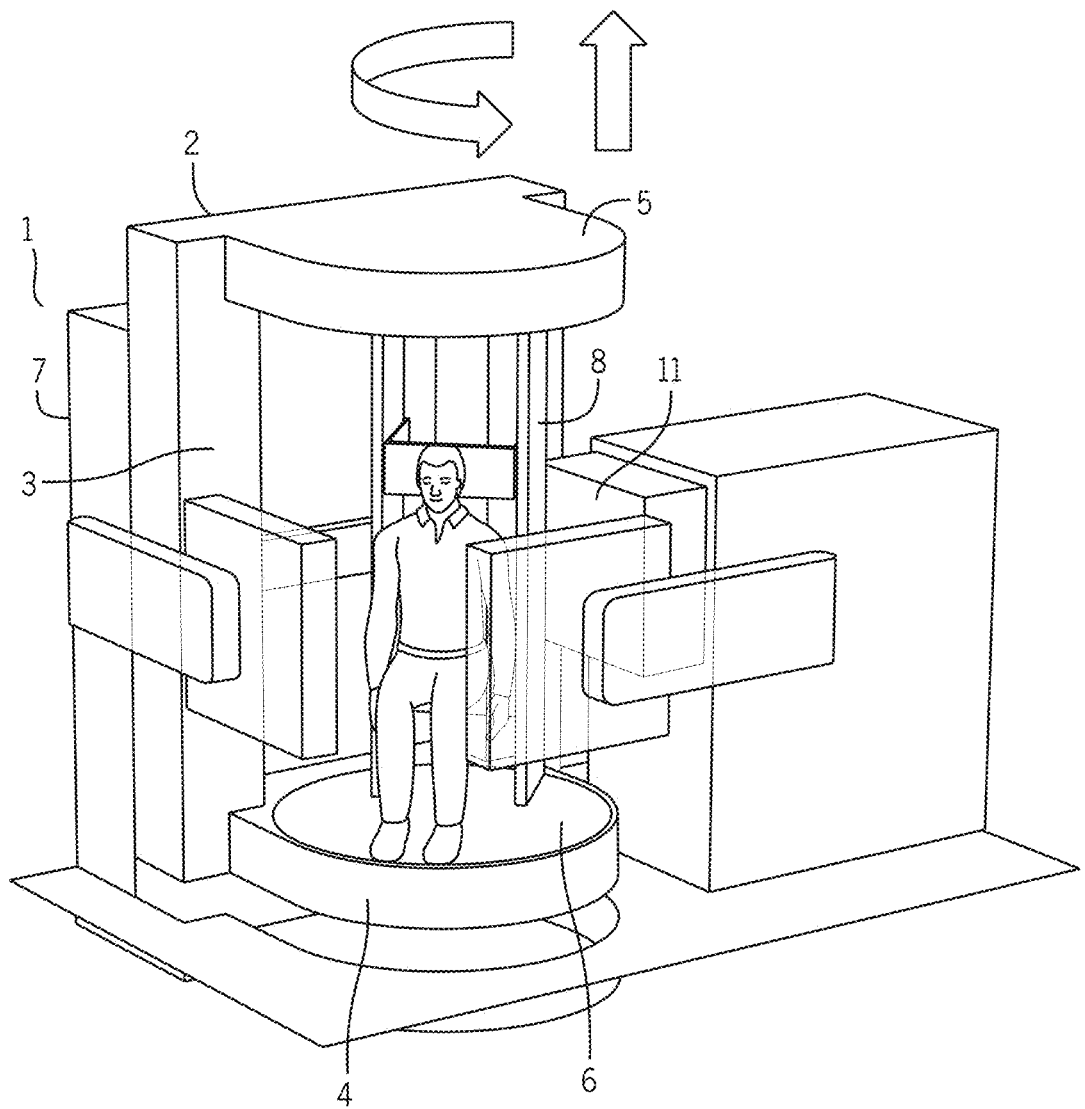
FIG. 4 illustrates the embodiment of FIG. 2 with the patient's position rotated and translated vertically upwards.

FIG. 4 shows the same embodiment of the patient positioning assembly 1 as FIGS. 2 and 3, with the translatable member 2 moved vertically upwards away from the first position so that the fixed treatment beam is able to target the relevant part of the patient's 9 torso.

Securing a patient 9 to the patient support 8 in a seated position allows for the fixed treatment beam to target a patient 9 in an area from the top of a patient's 9 head to the general region of the patient's 9 abdomen, for example the region of a patient's 9 navel. When in the first position, the treatment beam is configured to align with the seated patient's 9 head for a patient 9 with a height of 1900 mm. If a patient 9 is shorter than about 1900 mm, the treatment beam may be directed over the head of the seated patient 9 in the first position. To align such a patient's 9 head with the treatment beam, the translatable member 2 may be translated vertically upwards away from the surface 10 supporting the patient positioning assembly 1. Similarly, the patient 9 may be positioned vertically upwards by the translation of the translatable member 2 in order to align the fixed treatment beam with any part of the torso up to the general region of the patient's 9 navel. In order for the fixed treatment beam to target a part of the patient 9 lower than the navel, for example the legs, the patient 9 may be secured to the patient support 8 in a standing position rather than a sitting position, as shown in FIGS. 5 and 6.

Figure 5:
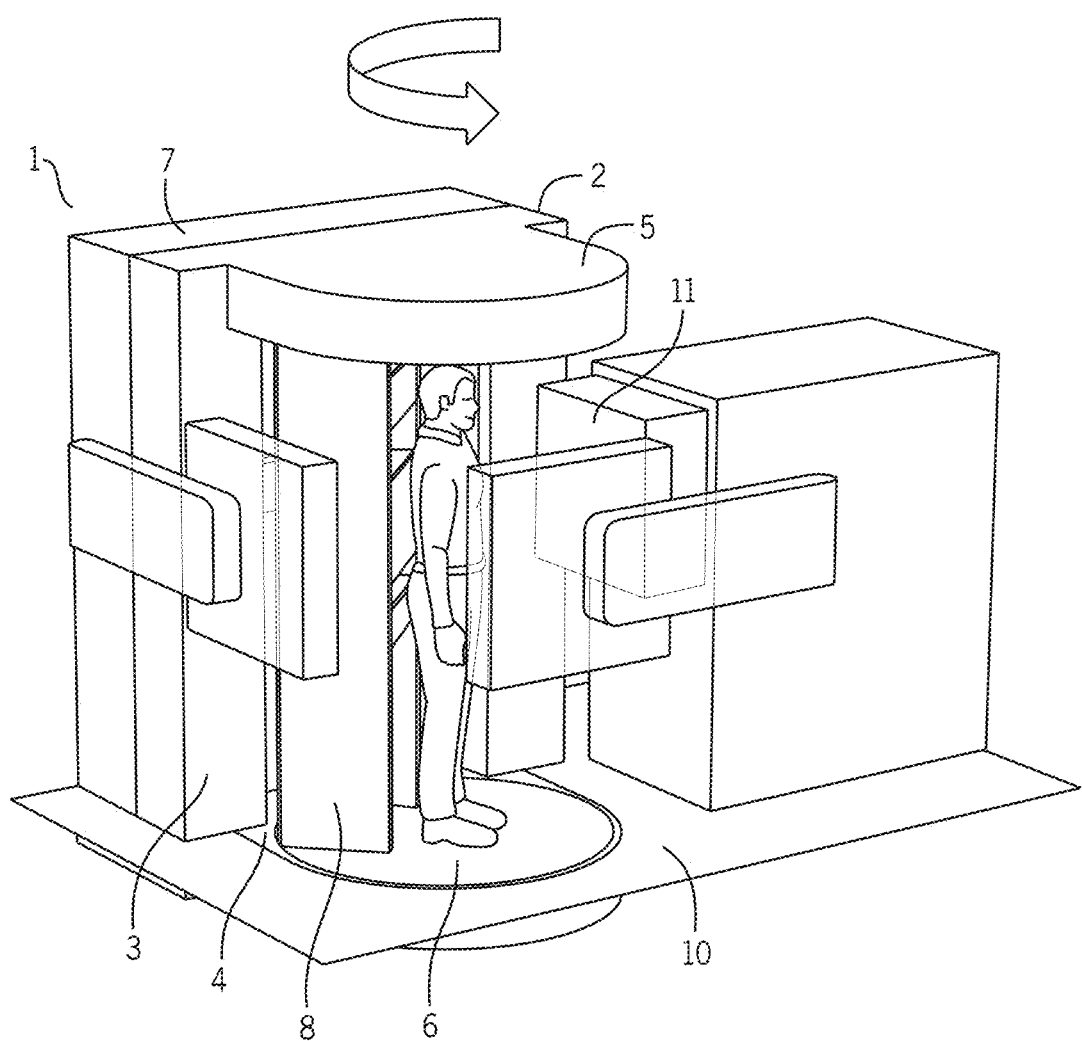
FIG. 5 illustrates the embodiment of FIG. 2 with the patient in a standing position.
Figure 6:
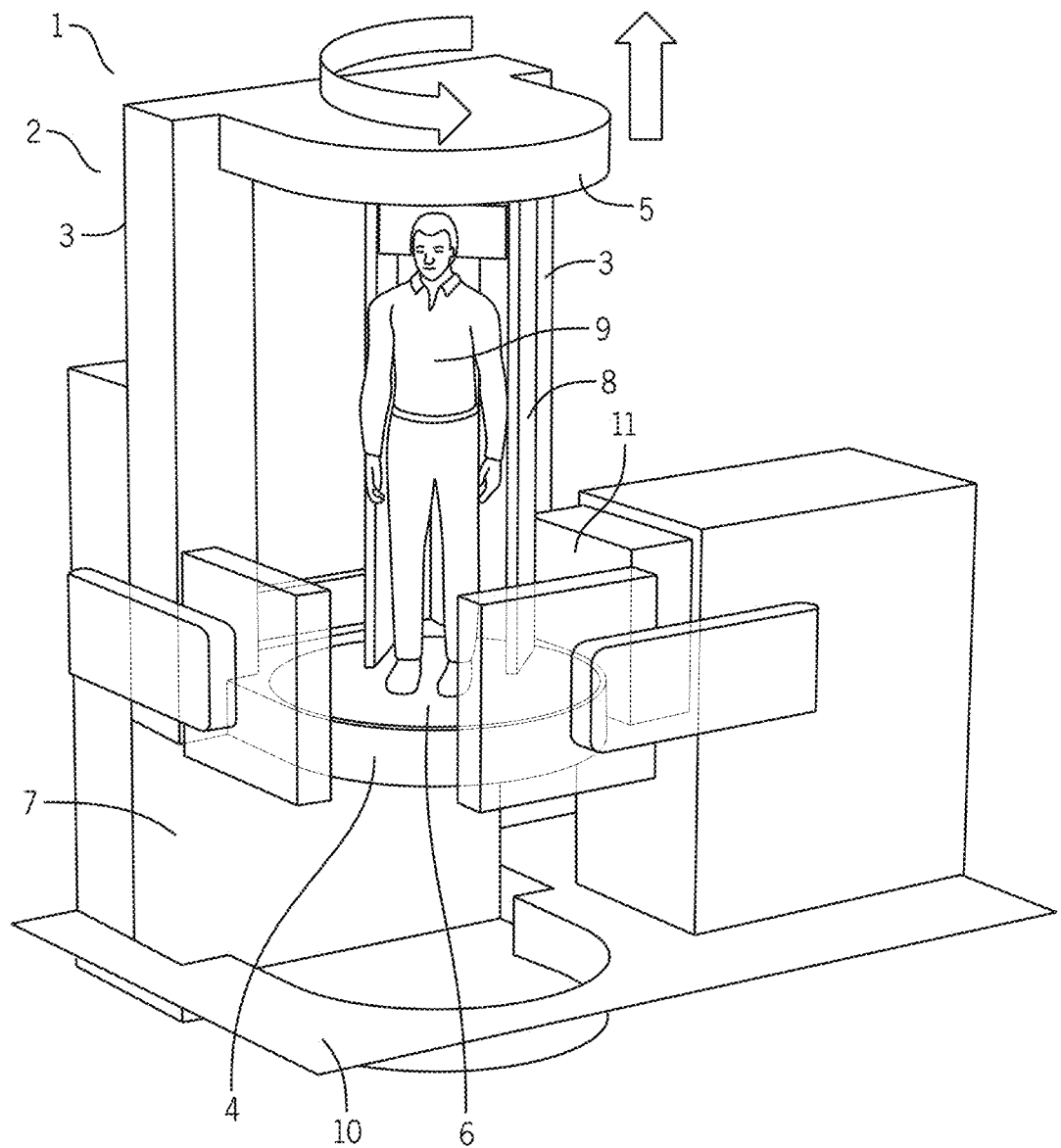
FIG. 6 illustrates the embodiment of FIG. 5 with the patient's position rotated and translated upwards.

FIG. 5 shows a standing patient 9 supported by the patient support 8 when the translatable member 2 is in the first position. The vertical height of the patient support 8 may be configured to accommodate a patient 9 with a height of about 1900 mm. FIG. 6 shows the translatable member 2 in a vertically upwards position termed the second position. When the translatable member 2 is in the second position, the fixed treatment beam may be directed towards the feet and/or ankle's of the patient 9, allowing treatment of this area. In order to align the fixed treatment beam with a section of the patient 9 between the patient's 9 feet and navel, the translatable member 2 may be moved to some appropriate vertical position between the first position and the second position.

The arrangement of FIGS. 1 to 6, allows for the fixed treatment beam to target any part of a patient 9, from the top of the head to the feet, while minimizing the vertical travel required by the translatable member 2. Minimizing the vertical travel required by the translatable member 2 in turn may reduce the vertical space required by the patient positioning assembly 1, thus allowing the assembly to be located in a smaller treatment bunker and reducing the costs of the assembly.

Figure 7:
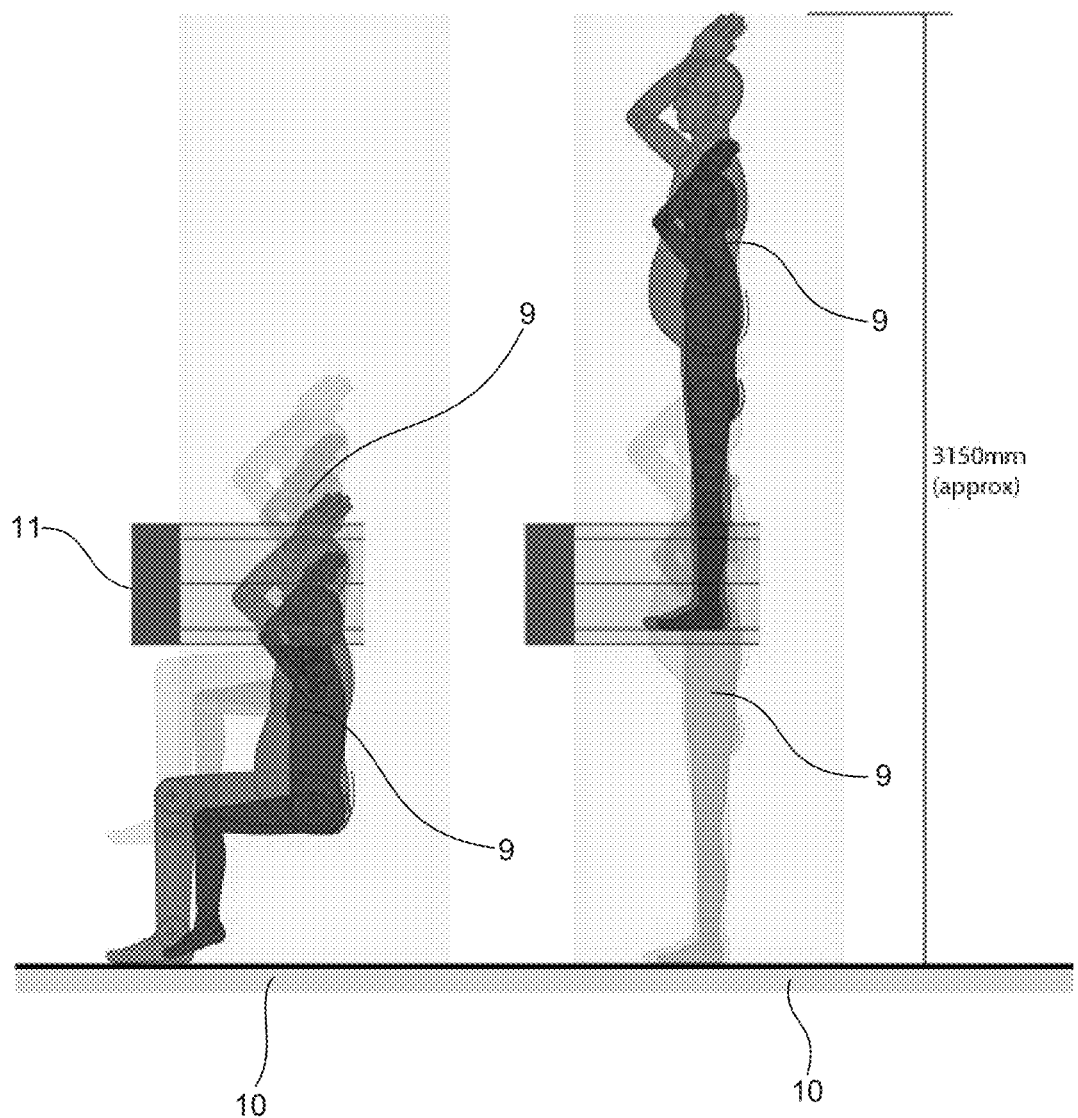
FIG. 7a illustrates a schematic view of the vertical translation required by the embodiment of FIG. 2 for a fixed treatment beam to target a seated patient between the heat and the region of the navel.
FIG. 7b illustrates a schematic view of the vertical translation required by the embodiment of FIG. 2 for a fixed treatment beam to target a standing patient up to the patient's feet.

FIGS. 7a and 7b demonstrate the translation height requirements of the arrangement of FIGS. 1 to 6. FIG. 7a shows a patient 9 in the 95$^{th}$ height percentile of an American male and a 5$^{th}$ height percentile of a Japanese female in a seated position in two vertical positions with respect to a fixed treatment beam. The two different positions indicate the amount of vertical translation required by the translatable member 2 to present a portion of a patient 9 between the top of the patient's 9 head and the region of a patient's 9 navel for treatment. FIG. 7b shows the same two patients 9 in a standing position with the translatable member 2 in both the first position and the second position, thus indicating the amount of vertical translation required for the fixed treatment beam to target the region of the patient's 9 foot. The total vertical translation required by the translatable member 2 is approximately 3150 mm in order for a 95$^{th}$ height percentile American male patient 9 in order to target any area of that patient 9 from head to foot.

As evident from the Figures, there may be some overlap in the parts of a patient 9 targetable by the fixed treatment beam whether the patient 9 is in a seated position or a standing position, for example, the lower torso. The amount of overlap may depend on the height of the patient 9. When the part of a patient 9 requiring treatment may be targeted in either of the standing or seated positions, the position in which the patient 9 is supported by the patient support 8 may be selectable, for example based on patient comfort, patient condition and/or treatment protocol.

Figure 8:
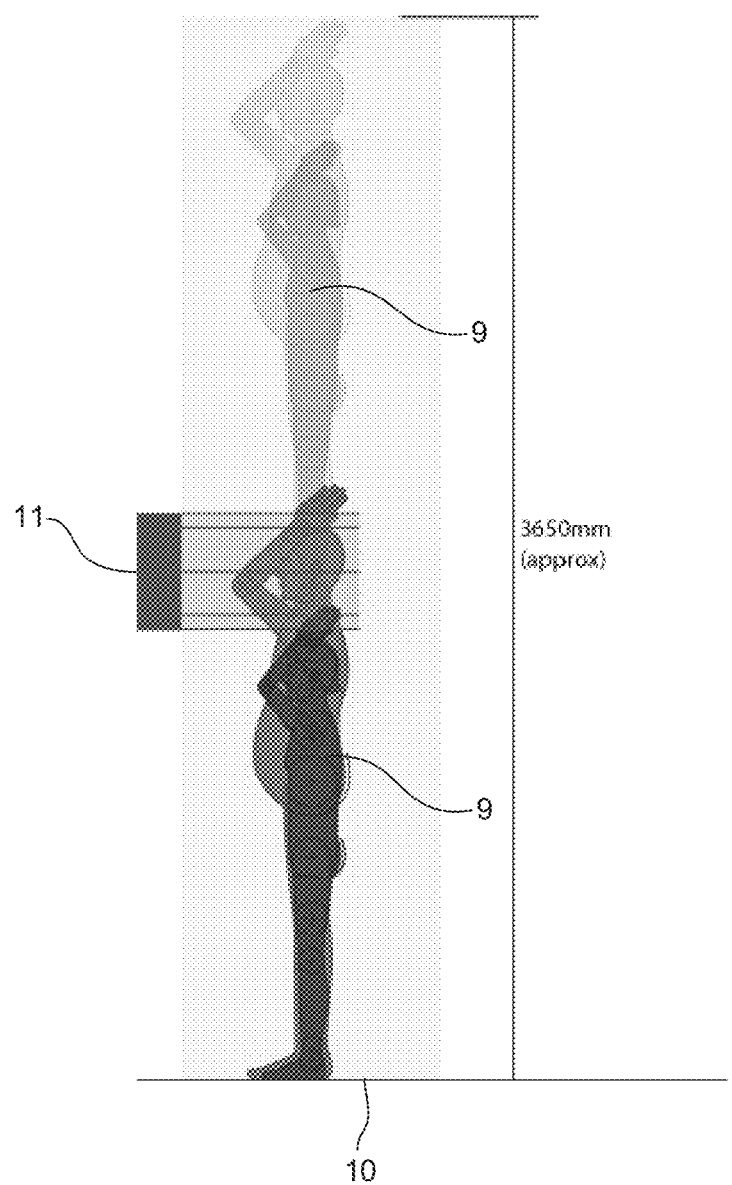
FIG. 8 illustrates a schematic view the vertical translation required by a fixed treatment beam to target a standing patient at any point between the head and feet for a comparison embodiment.

FIG. 8 demonstrates the height requirements of a comparative arrangement where the patient support 8 is only able to receive the patient 9 in a standing position. In such an arrangement, the first position is configured such that the treatment beam is aligned with a standing patient's 9 head, and the second position is configured such that the treatment beam is aligned with the standing patient's 9 feet. The arrangement of FIG. 8 would require that the translatable member 2 be able to translate vertically by about 3650 mm in order for the fixed treatment beam to be able to target any point between the head and the feet of an American male patient 9 of the 95$^{th}$ height percentile. As demonstrated by comparison of FIGS. 7a and 7b with FIG. 8, the patient positioning assembly 1 adaptable to receive patients 9 in both a seated and a standing position may reduce the vertical translation required for the fixed treatment beam to target the relevant part of the patient 9.

Figure 9:
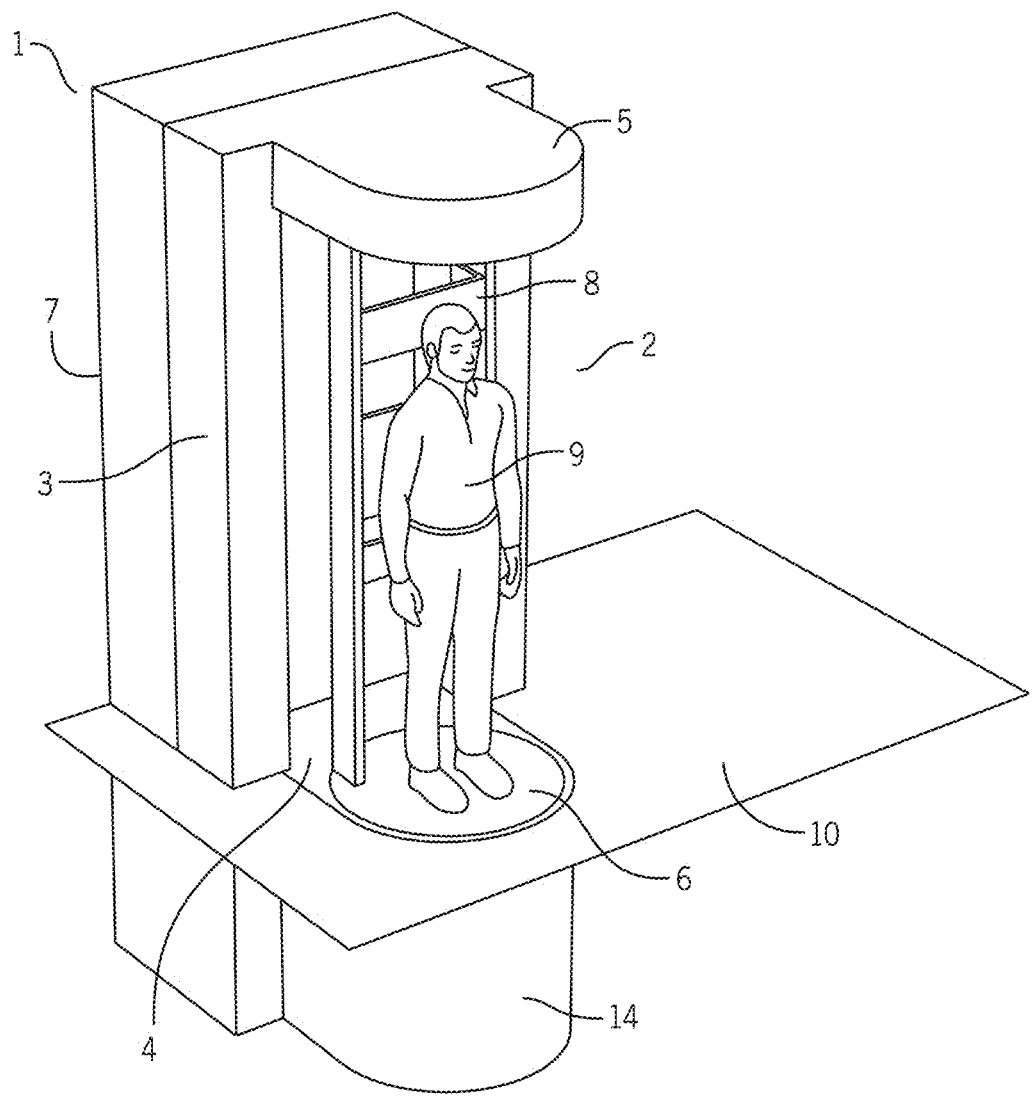
FIG. 9 illustrates an embodiment of a patient positioning assembly according to the present invention with a patient in a standing position.

FIG. 9 shows an embodiment of a patient positioning assembly 1 adapted to adjust the position of a patient 9 in a standing position only. The embodiment of FIG. 9 includes a translatable member 2, patient support 8 and supporting structure 7 similar to those of embodiments of FIGS. 1 to 6. However, the translatable member 2 is adapted to move between a vertically upwards second position and a vertically downwards first position wherein the translatable member 2 may locate in a recessed portion 14 of the surface 10 supporting the patient positioning assembly 1, such that part of the patient 9 positioned on the translatable member 2 may similarly locate in the recess 14. This arrangement may reduce the vertical height of the patient support 8 assembly by configuring a portion of the vertical travel of the translatable member 2 between the first and second positions into the surface 10 supporting the patient support 8 assembly. The embodiment of FIG. 9 shows the translatable member 2 in a vertical position between the first position and the second position where the first projection 4 of the translatable member 2 and the rotating disc 6 mounted thereto is substantially level with the supporting surface 10, allowing patient 9 access to the patient support 8 without having to negotiate an uneven surface.

Figure 10:
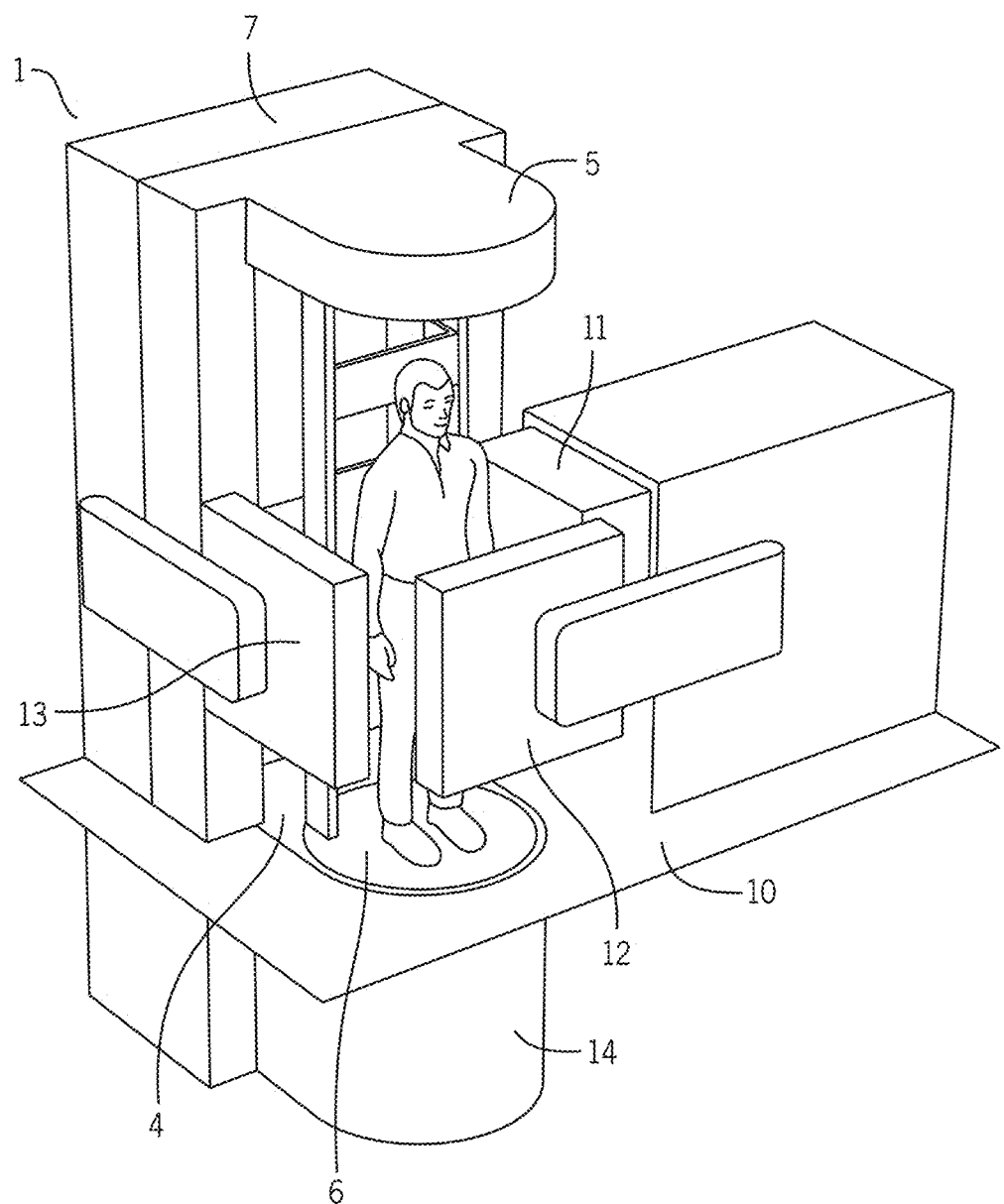
FIG. 10 illustrates the embodiment of FIG. 9 with a fixed treatment beam source and detection panels.

FIG. 10 shows the patient positioning assembly 1 of FIG. 9 in conjunction with a fixed beam source and detection panel 12.

Figure 11:
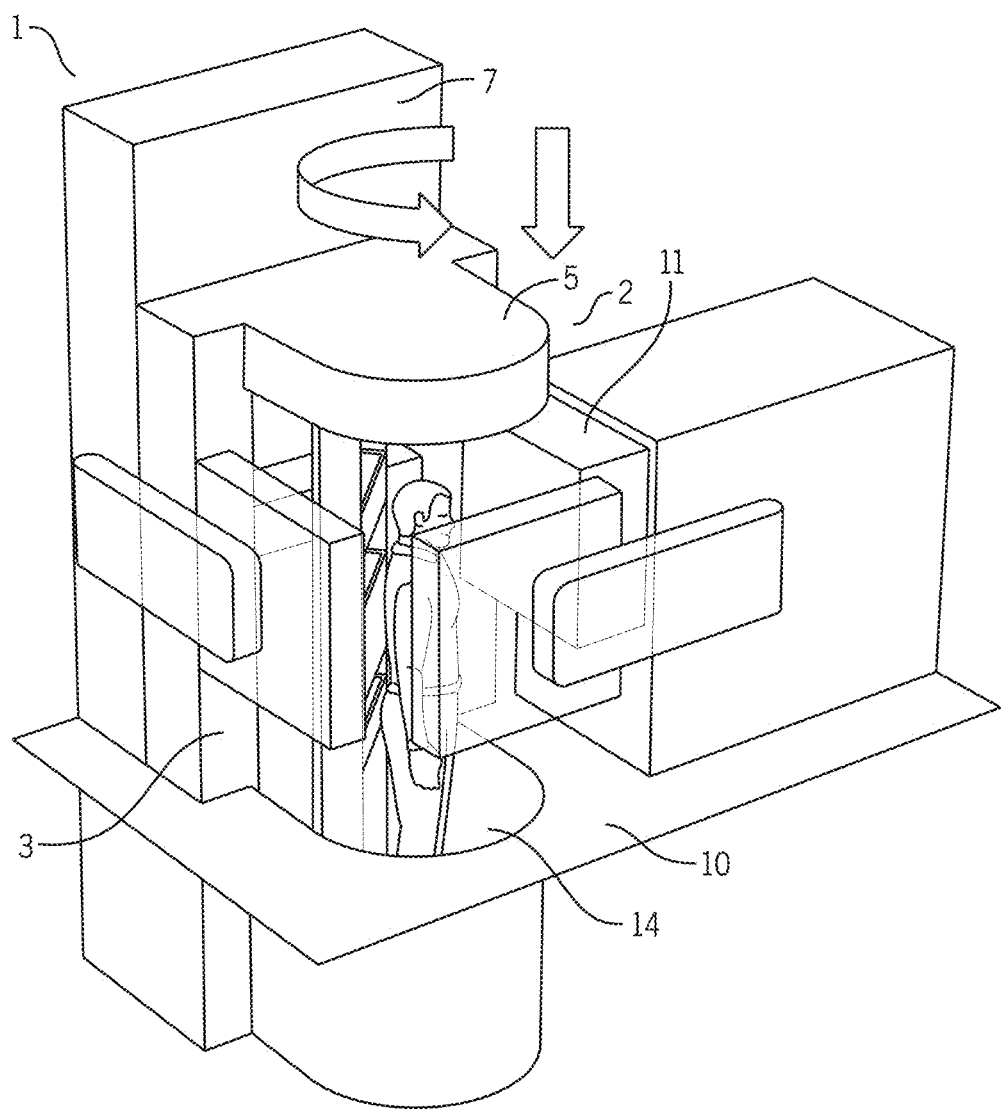
FIG. 11 illustrates the embodiment of FIG. 10 with the translatable member translated vertical downwards into a recess in the surface supporting the patient positioning assembly.

FIG. 11 shows the patient positioning assembly 1 of FIG. 10 where the translatable member 2 is in the first position partially located in the surface recess 14. Similarly, the lower portion of the patient 9 standing on the translatable member 2 is located in the recess 14. The patient positioning assembly 1 may be arranged so that the fixed treatment beam is directed towards the head of an American male of the 95$^{th}$ height percentile when that patient 9 is secured to the patient support 8 in a first position.

Figure 12:
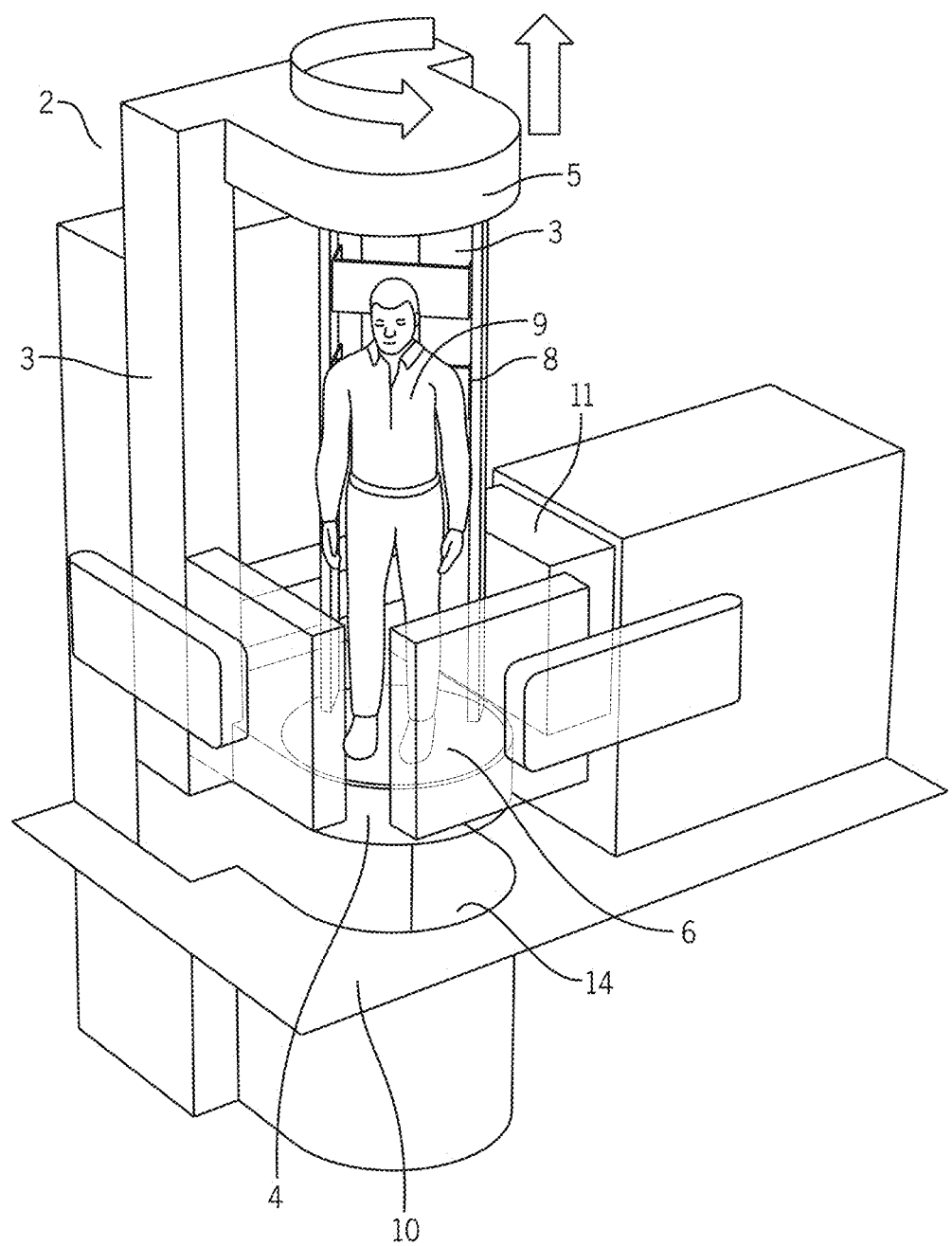
FIG. 12 illustrates the embodiment of FIG. 10 with the translatable member translated vertically upwards out of the recess and with the position of the patient rotated.

FIG. 12 shows that patient positioning assembly 1 of FIG. 11 where the translatable member 2 has been translated vertically upwards to the second positon. The patient positioning assembly 1 may be arranged so that the fixed treatment beam is directed towards the feet and/or ankles of a patient 9 secured to the patient support 8 in the second position.

Figure 13:
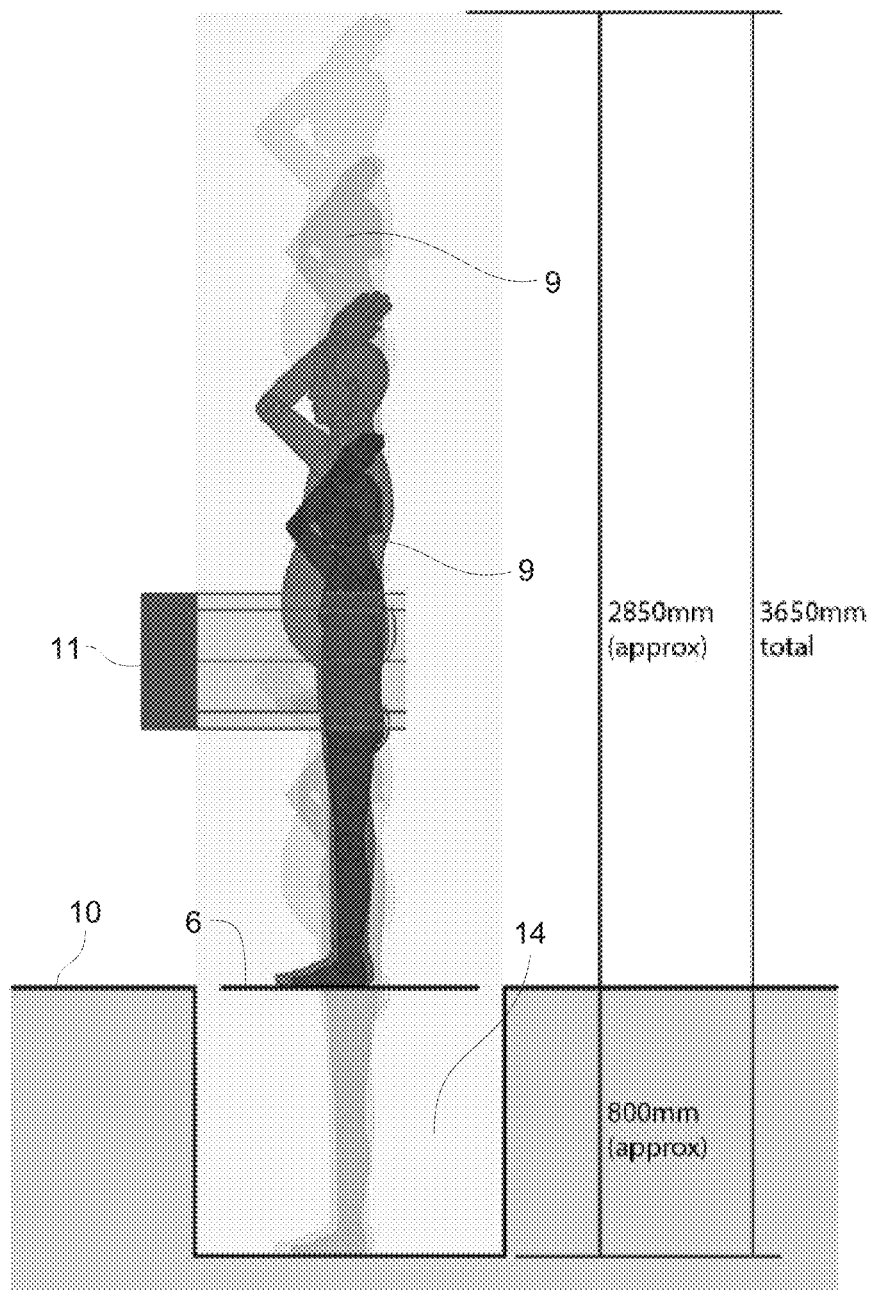
FIG. 13 illustrates a schematic view of the vertical translation required by the embodiment of FIG. 10 for a fixed treatment beam to target a patient at any point between the head and feet.

FIG. 13 demonstrates the height requirements for the patient positioning system of FIGS. 9 to 12 adapted to direct a fixed treatment beam from the head to the foot of an American male patient 9 of the 95$^{th}$ height percentile. The fixed treatment beam shown is a 400×400 mm treatment beam shaped by a multi-leaf collimator, though other treatment beam arrangements are equally permissible. The overall height of translation required is the same as the positioning system of FIG. 8. However, configuring the translatable member 2 to locate in a recess 14 in the surface 10 supporting the assembly, such that the translatable member 2 may translate 800 mm vertically downwards from the surface 10 when in the first position, may reduce the upward vertical travel of the translatable member 2 in the second position to about 2850 mm from the surface 10. By this arrangement, the patient positioning assembly 1 may be able to be located in existing structures or bunkers with a lower ceiling height. In other embodiments, the depth of the recess 14 may be more or less that 800 mm, with an associated effect on the height of extension of the translatable member 2 from the floor in the second position.

Figures 14A, 14B:
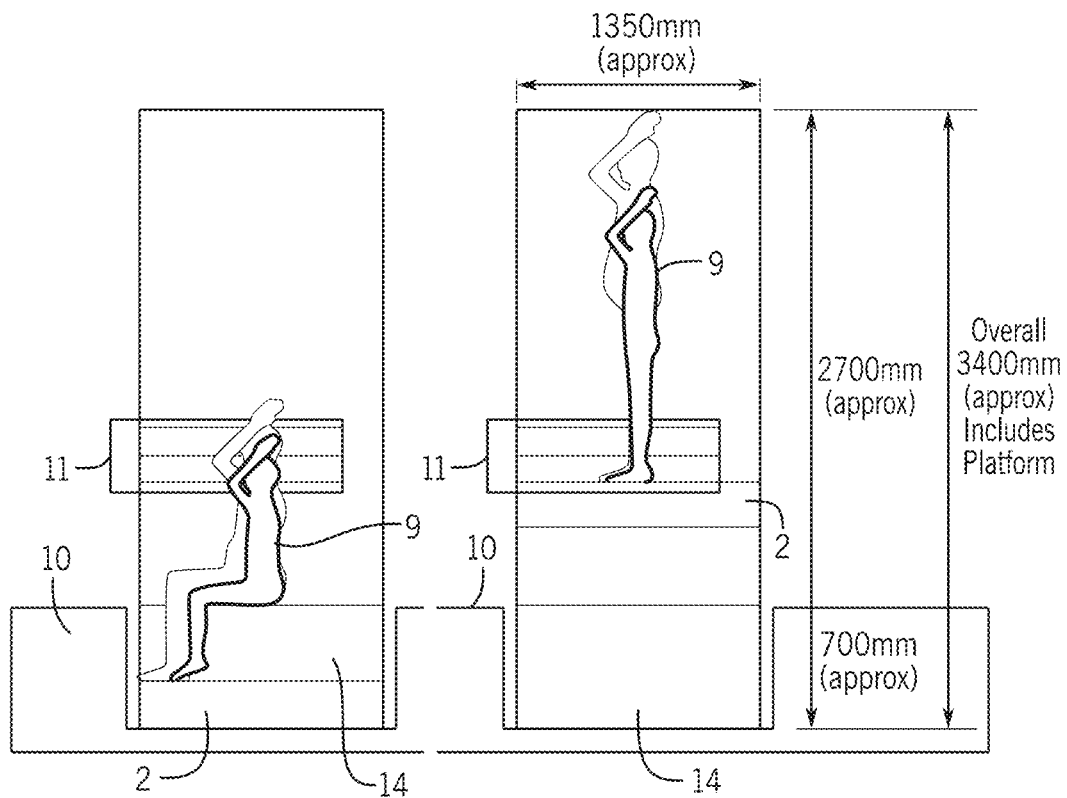
FIG. 14a illustrates a schematic view of an embodiment with the translatable member in the first position located in a recess with a fixed treatment beam targeting the head of a seated patient.
FIG. 14b illustrates a schematic view of an embodiment with the translatable member in the second position with a fixed treatment beam targeting the ankles/feet of a standing patient.

FIGS. 14a and 14b show an alternative embodiment of the patient positioning assembly 1 where the patient 9 may be orientated in both a sitting and a standing position and wherein the translating member 2 may partially locate in a recess 14 in the surface 10. This arrangement combines certain benefits of the embodiments of FIGS. 1 to 7 and FIGS. 9 to 13 by both configuring a portion of the vertical travel of the translatable member 2 into the recess 14, and by allowing the patient 9 to be mounted to the patient support 8 in both the sitting and standing position. FIG. 14a shows a seated patient 9 in the first position wherein a lower portion of the translatable member 2 is located in a recess 14 with an approximate depth of about 700 mm such that a portion of the seated patient's 9 legs are also located in the recess 14. In order for the fixed treatment beam to target the head of a patient 9 with a height of about 1900 mm when seated in the first position, the fixed treatment beam source 11 may be located nearer to the surface 10 than the embodiment of FIGS. 1 to 7.

FIG. 14b shows the standing patient 9 in the second position where the translatable member 2 has been translated vertically upwards out of the recess 14, so that the feet and ankles of the patient 9 are aligned with the fixed treatment beam, thereby allowing this region of the patient 9 to be treated. The standing position of the patient in FIG. 14b may also allow the region of the patient 9 between the navel and the knees to be treated when the translatable member 2 is between the first and second position, as the seated position would align the thighs of the patient 9 in the same plane as the treatment beam thus making treatment unsuitable.

By locating a portion of the vertical travel of the patient positioning assembly 1 into a recess 14 in the surface 10, the patient positioning assembly 1 of FIGS. 14a and 14b may require less physical space in the vertical direction measured from the surface 10 thereby making this embodiment suitable for rooms/bunkers with a lower ceiling.

Figures 15A, 15B:
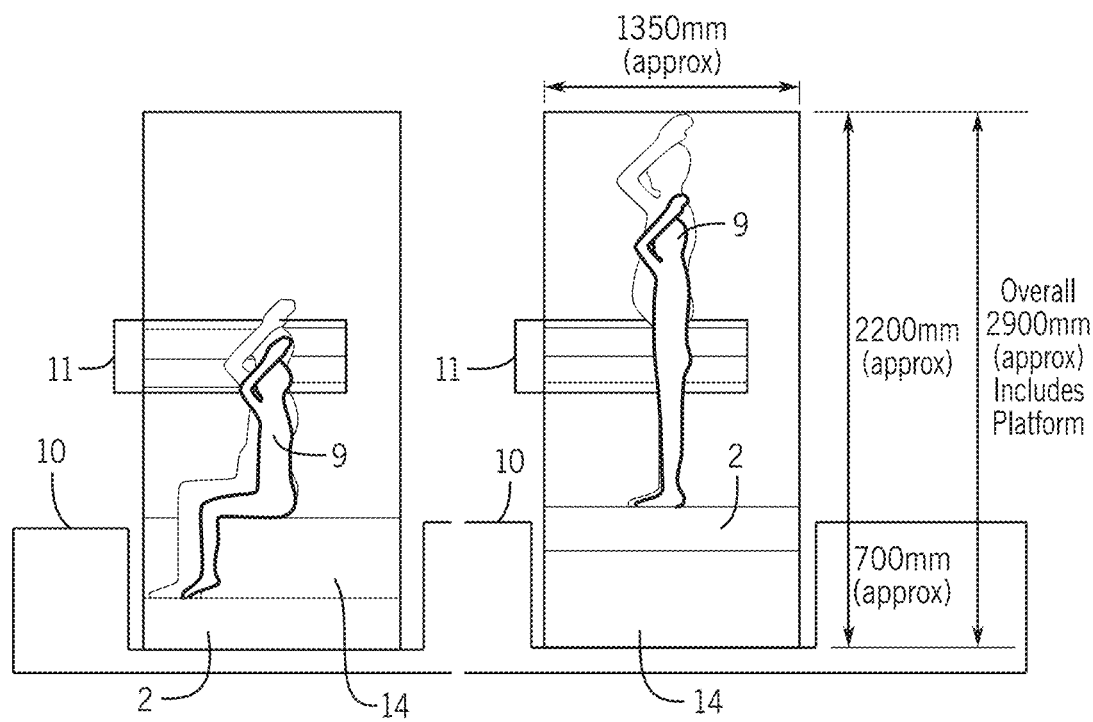
FIG. 15a illustrates a schematic view of an embodiment with the translatable member in the first position located in recess with a fixed treatment beam targeting the head of a seated patient.
FIG. 15b illustrates a schematic view of an embodiment standing patient with the translatable member in a second position with a fixed treatment beam targeting the thighs of a standing patient.

FIGS. 15a and 15b show an alternative embodiment of the patient positioning assembly 1 where only a portion of the patient 9 is positionable in alignment with the fixed treatment beam. FIG. 15a shows a patient 9 seated on a translatable member 2 in the first position in the same manner as FIG. 14a, with the fixed treatment beam directed towards the head of a patient 9 of 1900 mm height. FIG. 15b shows the patient 9 in a standing position on a translatable member 2 in the second position, configured such that the fixed treatment beam may be directed toward the thigh region of a female Japanese patient 9 of the 5$^{th}$ height percentile which is about 1490 mm. By configuring the assembly so that the fixed treatment beam is directed towards the head of a seated patient 9 of 1900 mm height in the first position, and towards the thighs of a patient 9 of 1490 mm height in the second position, the embodiment of FIG. 15 is accordingly able to target an area between a patient's 9 head and thighs for a wide population of patient 9 heights. Such an arrangement may require less physical space in the vertical direction and allow the fixed treatment beam to target the most common areas of a patient 9 requiring treatment.

In an alternative embodiment, the patient positioning assembly 1 may be adapted such that a patient 9 is securable to the patient support 8 in a seated position only. In this embodiment, the first position of the translatable member 2 may be configured to align the head of a patient 9 with the fixed treatment beam 11, and the second position may be configured to align the lower torso of the seated patient 9 with the fixed treatment beam 11. This embodiment would be suitable for aligning a portion of the patient 9 between the head and the navel with the fixed treatment beam 11, allowing the treatment beam to target these common treatment areas and minimizing the upward vertical movement required by the translating member 2 and also minimizing the vertical height occupied by the patient positioning assembly 1.

Figure 16:
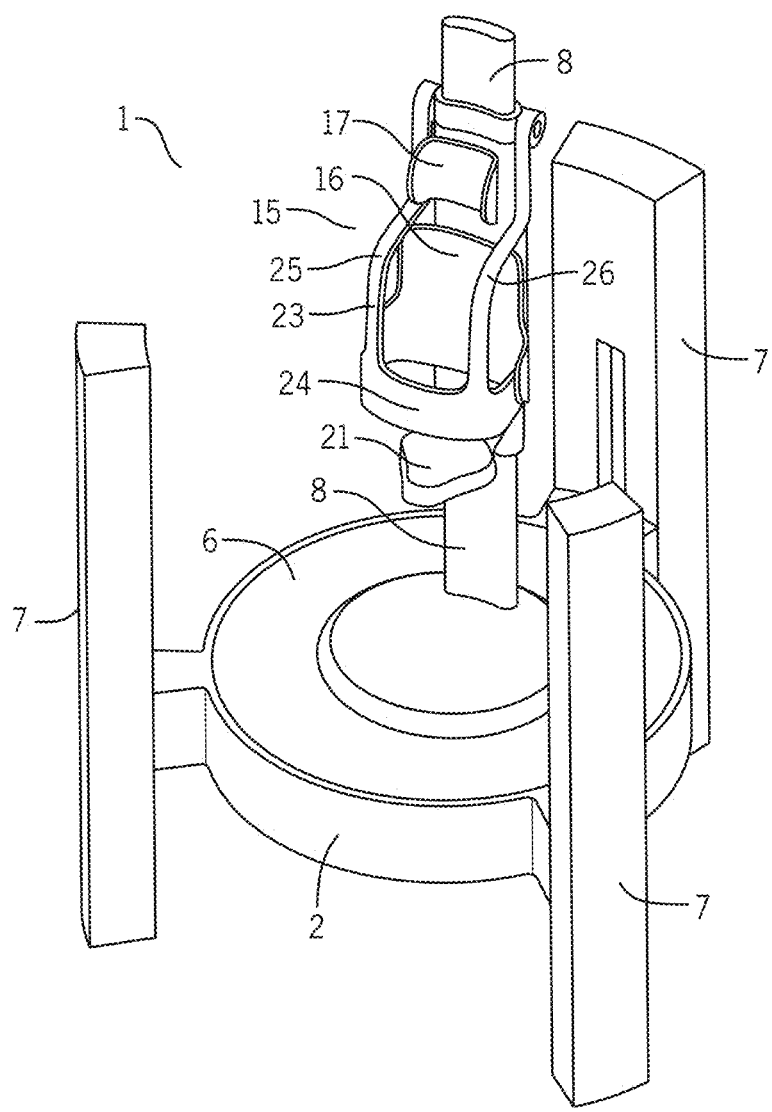
FIG. 16 illustrates an alternative embodiment of the patient positioning assembly according to the present invention.

FIG. 16 shows an alternative embodiment of the patient positioning assembly 1. This embodiment may be adapted to receive a patient 9 in either the standing or the seated position, and may be adapted to partially locate in a recess 14 in order to reduce height requirements of the assembly. The supporting structure 7 of the patient positioning assembly 1 is in the form of three pillars arranged about the translatable member 2 which is in the form of a circular platform. The translatable member 2 may operatively connect with the pillars, which provide support to the translatable member 2. One or more of the pillars may also incorporate a drive mechanism to affect the vertical translation of the translatable member 2 relative to the pillars. In an alternative embodiment, the drive mechanism may be located in the circular platform of the translatable member, though other arrangements are possible. A patient support 8 may be mounted to a rotating disc 6 which is in turn rotatably mounted to the translatable member 2 such that the patient support 8 may rotate about a vertical axis. The patient support 8 is in the form of a rigid elongate structure configured to receive a patient 9 in a generally upright position, and may be orientated in parallel alignment with the vertical axis of rotation. The patient support 8 may also include a pedestal adapted to support the feet of a standing patient 9. The elongate axis of the patient support 8 may be offset from the vertical axis such that a patient 9 secured to the patient support 8 may have their torso centered about the vertical axis. A patient restraint system 15 may be mounted to the patient support 8 for securing the patient 9 into position against the patient support 8.

Figure 17:
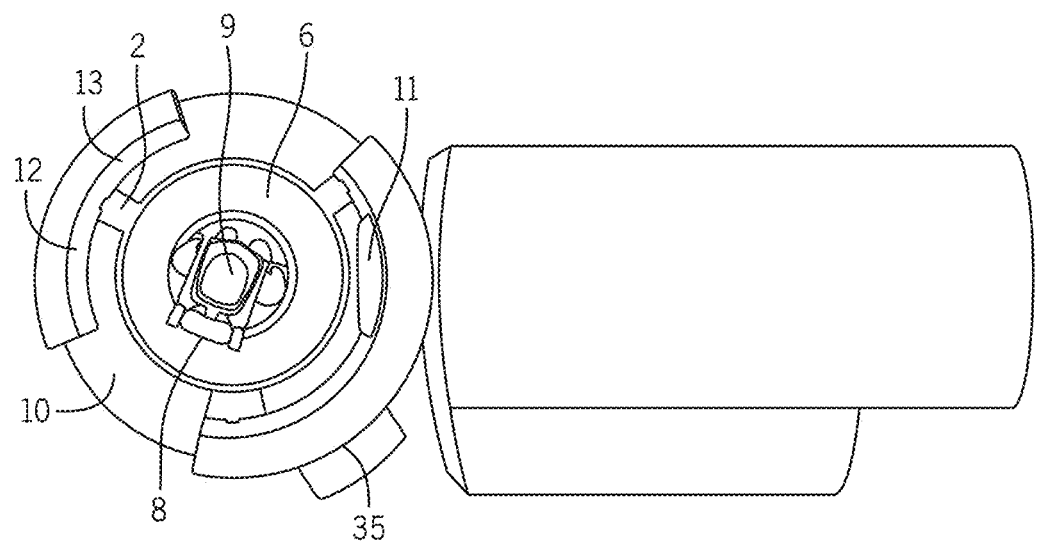
FIG. 17 illustrates a plan view of the embodiment of FIG. 16 with a fixed beam source, a fixed imaging beam source and associated detection panels.

FIG. 17 shows a plan view of the patient positioning assembly 1 in conjunction with a fixed treatment beam source 11 and detection panel 12. Also shown is an imaging beam source 35 and associated additional detection panel 13. Both the treatment beam and imaging beam may be orientated in the same horizontal plane and may both intersect with the vertical rotation axis.

Figure 18:
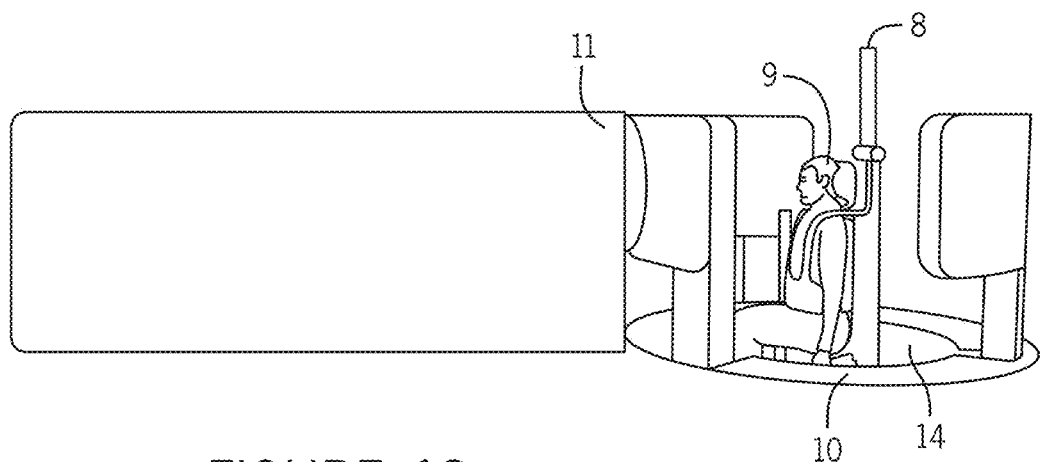
FIG. 18 illustrates a side view of the embodiment of FIG. 17 with a patient in a seated position and with the translatable member translated vertically downwards into a first position locating in a recess in the surrounding surface.
Figure 19:
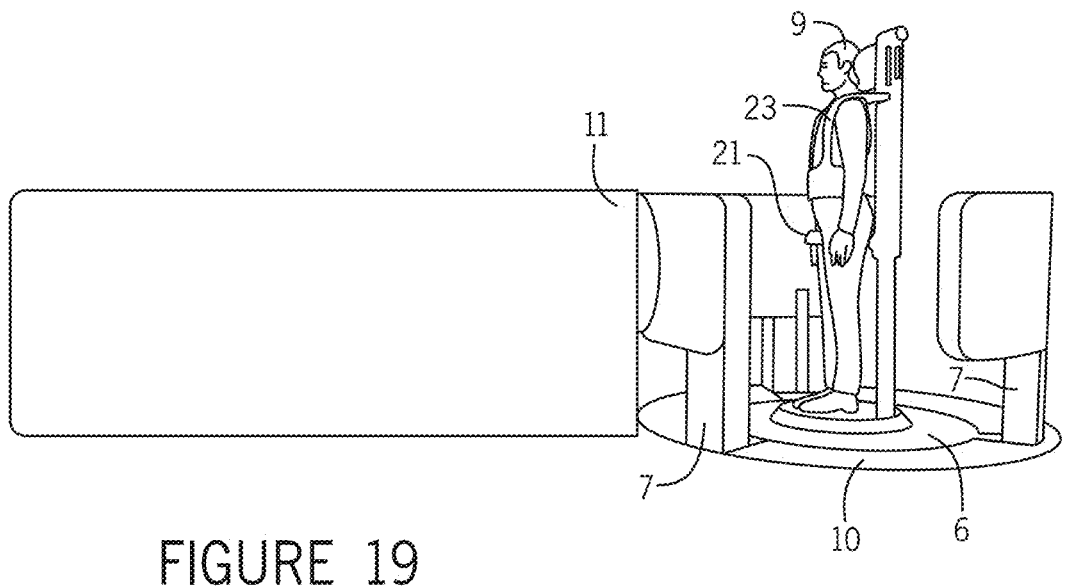
FIG. 19 illustrates the embodiment of FIG. 18 with a patient in a standing position and with the translatable member in a position between the first position and the second position.
Figure 20:
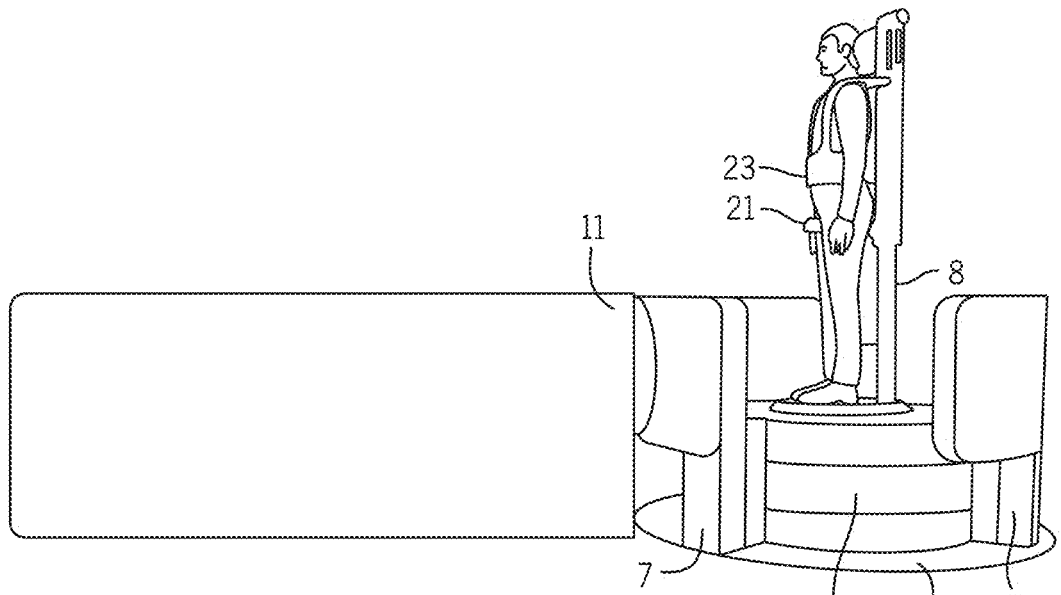
FIG. 20 illustrates the embodiment of FIG. 18 with a patient in a standing position and with the translatable member in a second position.
Figure 21:
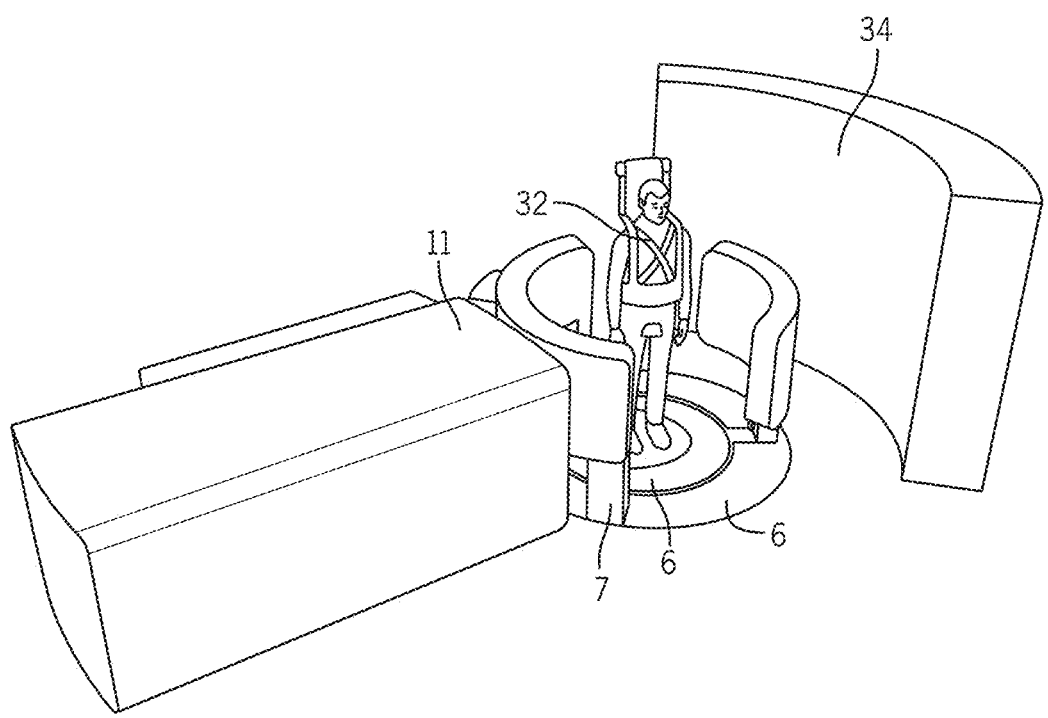
FIG. 21 illustrates a perspective view of the embodiment of FIG. 18.

FIG. 18 shows a side view of the arrangement of FIG. 17. The translatable member 2 has been translated vertically downwards into the first position with the translatable member 2 and the lower portion of the patient 9 locating in a recess 14 in the surface 10. The first position of the patient positioning assembly 1 may be configured so that the fixed treatment beam is directed towards the head of a seated patient 9. FIG. 19 shows the arrangement of FIG. 18 wherein the translatable member 2 is in an intermediate position between the first position and the second position, with the upper surface of the translatable member 2 and the rotating disc 6 being substantially level with the surface 10. FIG. 20 shows the arrangement of FIG. 19 with the translatable member 2 moved vertically upwards into the second position wherein the feet and ankles of the standing patient 9 are aligned with the fixed treatment beam. FIG. 21 shows a perspective view of the embodiment of FIG. 20 as well as a radiation shield 34. As the fixed treatment beam is stationary in position, radiation shielding 34 need only be placed in a single location in the treatment beam path.

Figure 22:
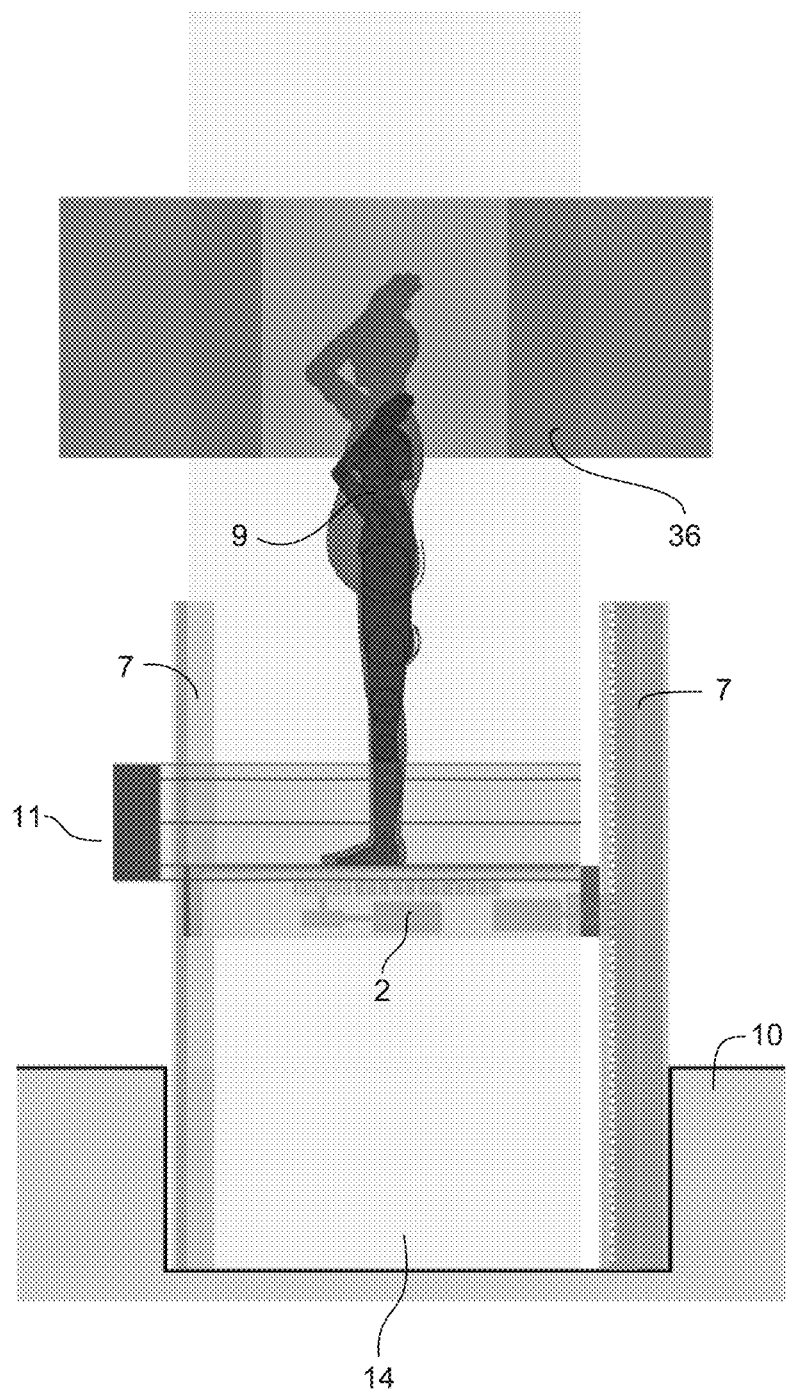
FIG. 22 illustrates a schematic view of a patient positioning assembly and CT scanner located vertically above the patient positioning system, with a patient in a standing position and a translatable member in a second position.
Figure 23:
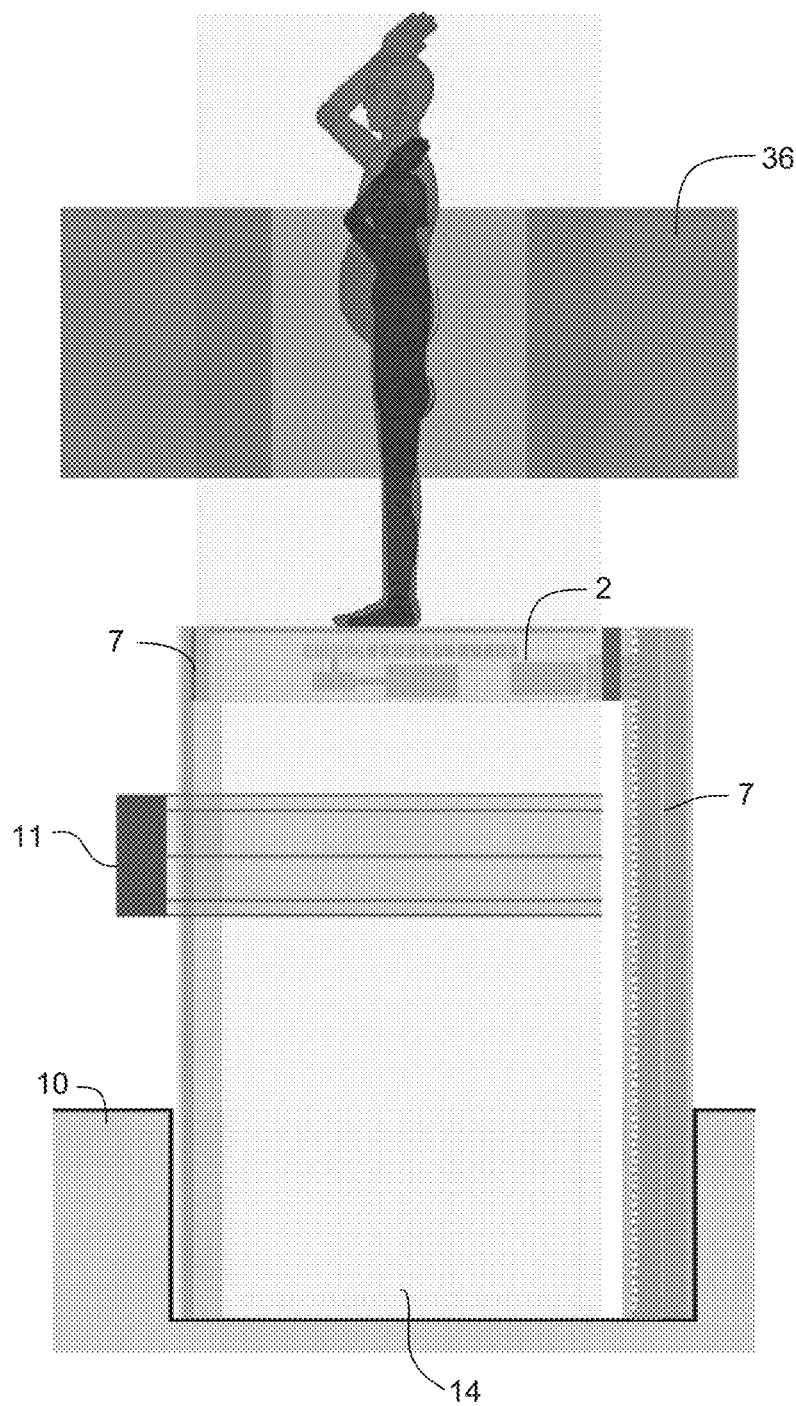
FIG. 23 illustrates a schematic view of the embodiment of FIG. 22 with the translatable member vertically translated above the second position with a standing patient locating in the CT scanner.

Referring to FIGS. 22 and 23, shown is an embodiment of the patient positioning assembly 1 where an imaging system 36 such as a CT scanner 36 is located vertically above the patient positioning assembly 1. By locating the patient positioning assembly 1 vertically adjacent with the imaging system 36, the patient positioning assembly 1 may be used to orientate the patient 9 with respect to both the fixed treatment beam as well as the imaging system 36. This arrangement may also allow the patient 9 to be imaged by the imaging system 36 in a upright position, providing medical professionals with images of the patient's 9 anatomy in the upright position in which they will be subjected to the fixed treatment beam, thus reducing uncertainties that may arise from the gravitational shifting of a patient's 9 anatomy if imaging is performed in a different patient 9 position to treatment.

FIG. 22 shows a standing patient 9 secured to the translatable member 2 in the second position with the feet and ankles of the patient 9 in view of the fixed treatment beam. In this position, a taller patient 9 may partially locate in the imaging chamber of a CT scanner 36, although a shorter patient 9 may not. FIG. 23 shows the translatable member 2 moved upwards in a position beyond the second position wherein a midsection of the patient 9 may locate in the CT scanner 36.

In the embodiments hereinbefore described, the radiation source in the form of a treatment beam is fixed in position such that the relative movement between the patient and the treatment beam is effected by the movement of the patient positioning assembly. In an alternative embodiment, the position of the treatment beam may be adjustable such that the relative movement between the patient and the treatment beam may be effected by the movement of the patient positioning assembly as well as by adjusting the position of the treatment beam. For example, the position of the treatment beam may be adjustable between two vertically displaced positions such that the vertical travel required by the patient support assembly may be reduced and instead accounted for by the vertical adjustment of the treatment beam. If the degree of adjustment of the treatment beam is relatively small, the additional shielding required may be minimized.

Although the embodiments hereinbefore described relate to a radiation source in the form of a treatment beam source, and more specifically, a liniac shaped by a multi-leaf collimator, it is to be understood that the patient positioning assembly may be used with other forms of radiation sources, for example imaging technologies such as CT scanners or MRI.

A patient restraint system 15 may be mounted to the patient support 8 in order to securely and comfortably restrain the patient 9 to the patient support 8. The patient restraint system 15 for the patient positioning assembly 1 of FIGS. 1 to 6 and FIGS. 16 to 21 may be adaptable into a first orientation where the patient restraint system 15 is configured to secure the patient 9 to the patient support 8 in a seated position, and a second orientation where the patient restraint system 15 is adapted to secure the patient 9 to the patient support 8 in a standing, or in a substantially standing, position. The patient positioning assembly 1 of FIGS. 9 to 12 only requires the patient restraint system 15 to secure the patient 9 to the patient support 8 in a standing position.

Shown in FIGS. 24 to 29 are an embodiment of a patient support assembly 41 that may be suitable for use with embodiments of the patient positioning assembly 1 described herein. The patient support assembly 41 may be adapted to receive and support a patient 9 with a torso tilted at an angle to the vertical axis. By this arrangement, the effect of gravity acting on the tilted orientation of the patient relative to a vertical axis may aid in stabilizing the patient received by the patient support assembly. The patient's torso may be tilted anteriorly, or posteriorly as depicted. A patient received by a patient support with their torso angled with respect to a vertical axis in an anterior direction may facilitate targeting of a patient's breasts by a radiation source. The angle by which the patient's torso is configured to tilt may be between about ±0° to about 20°, between about ±5° to about 15°, or about ±10°. The patient support assembly 41 may be configured to receive a patient 9 with a torso tilted at an angle in both a first orientation, or a first configuration, wherein the patient is in a generally seated position, and a second orientation, or a second configuration, wherein the patient is in a generally standing, or substantially standing, position. In an embodiment, a patient in the second orientation may be received by the patient support assembly in a generally standing position with a torso angled with respect to a vertical axis, which may be termed a perched position. Such a generally standing, or perched position, may further involve the patient having bent knees as depicted in FIG. 24*b*.

Figures 24A, 24B:
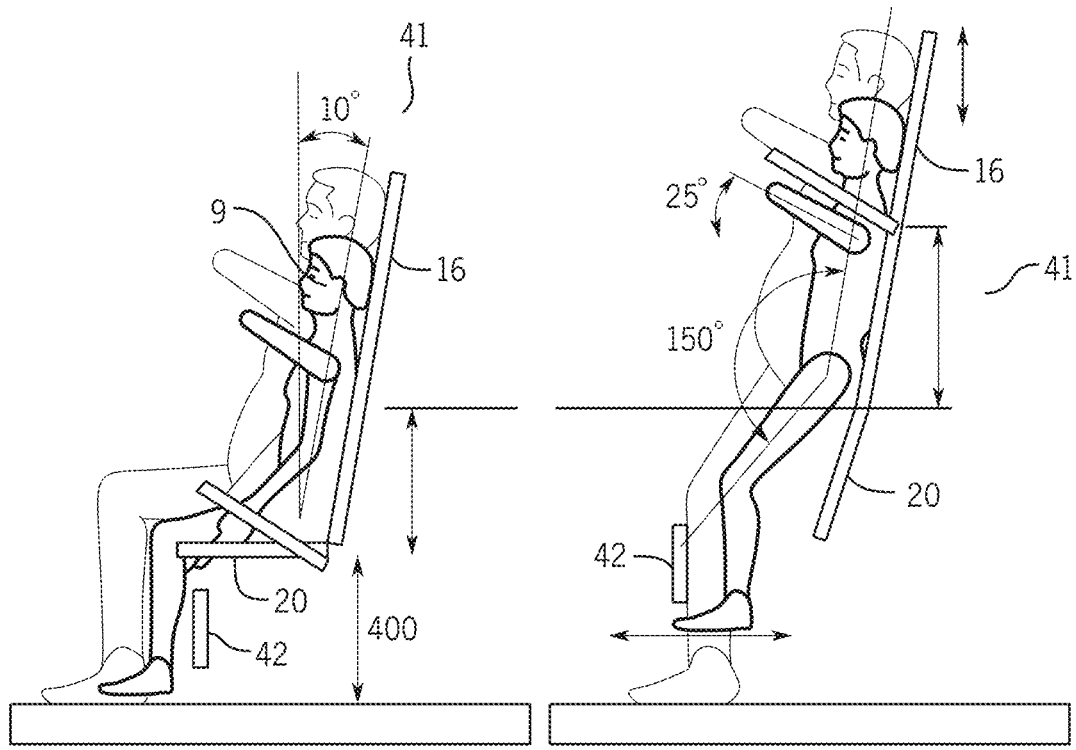
FIG. 24a illustrates a schematic view of an embodiment of a patient support assembly in a first orientation.
FIG. 24b illustrates a schematic view of an embodiment of a patient support assembly in a second orientation.

FIG. 24*a* shows an embodiment of a patient support assembly 41 in a first orientation configured to receive a patient 9 in a generally seated position. In the embodiment of FIG. 24*a*, two patients are depicted; one with height equivalent to the 95$^{th}$ percentile of an American male and the other with a height equivalent to the 5$^{th}$ percentile of a Japanese female, demonstrating the efficacy of the patient support assembly 41 for a wide spectrum of the patient population. The patient support assembly 41 may include a back rest 16 which may be angled with respect to a vertical axis such that a patient 9 resting their back thereagainst may similarly have their torso angled with respect to a vertical axis. The patient support assembly 41 in the first orientation may further include a seat member 20 extending from a plane generally aligned with the back rest for accommodating the buttocks, or posterior, of a patient 9 in a seated position. The patient support assembly 41 in the first orientation may further include a shin rest 42 positioned toward the back rest 16 so as to situate posterior to the patient's ankles thereby not contacting with any part of the patient 9 in the seated position. In an embodiment, the shin rest 42 may situate underneath the seat member 20 when the patient support assembly 41 is in the first orientation. The patent support assembly 41 may further include arm rests 18, which may be adjustable in location along the axis of the back rest 16. Adjusting the vertical position of the arm rests 18 along the axis of the back rest 16 may allow patients with varying anthropometric variation to comfortably rest their arms in a number of differing positions to facilitate specific target areas being targeted by a radiation source 11.

FIG. 24*b* shows an embodiment of a patient support assembly 41 in a second orientation configured to receive a patient 9 in a generally standing position. In the configuration of the second orientation, the posterior lean of the back rest 16 is maintained and displaced vertically upwards to receive the back of a patient 9 in a generally standing position having their knees bent. The seat member 20 may be removed from the assembly, folded downwards toward alignment with the plane of the back rest, or otherwise displaced from its position in the first orientation so as to not provide an obstacle to a patient 9 received by the patient support 41 in the second position. In one embodiment (not depicted), the seat member 20 may be located posteriorly of the patient's thighs thus providing support for the patient's upper legs in a generally standing position with bent knees. The patient support assembly 41 in the second orientation may further include a shin rest 42 anterior of the patient's ankles so as to locate against the patient's shins in the generally standing position. By this arrangement, the shin rest 42 may support the weight of the patient's shins with the patient's back supported by the back rest 16. In an embodiment, the shin rest 42 may be adapted to receive the patient's shins with the ankles in generally vertical alignment, though other arrangements are possible. In the depicted embodiment, the shin rest 42 may be positioned such that a patient 9 in a generally standing position with a torso inclined 10° with respect to a vertical axis may have their hips bent at an angle of about 150° as measured between the torso and the thighs. Such a configuration may allow a patient 9 to remain still and comfortable in a generally standing position with bent hips and knees while having their weight supported by the back rest 16 and the shin rest 42. In other embodiments the hips may be bent at an angle of between about 135° to about 165°, between about 145° to about 155°, or by some other suitable angle. Selection of the hip angle may depend on several factors including the size of the patient, the angle of posterior incline of the patient's torso, and patient comfort and/or range of mobility. In the depicted embodiment, the position of the adjustable arm rests 18 are selected such that the patient's upper arms are at an angle of about 25° relative to a horizontal plane orthogonal to the vertical axis of rotation. Such a position may allow a patient to comfortably and stably support their arms in a position above their chest to allow the chest area to be targeted by a radiation source 11.

Figure 25A:
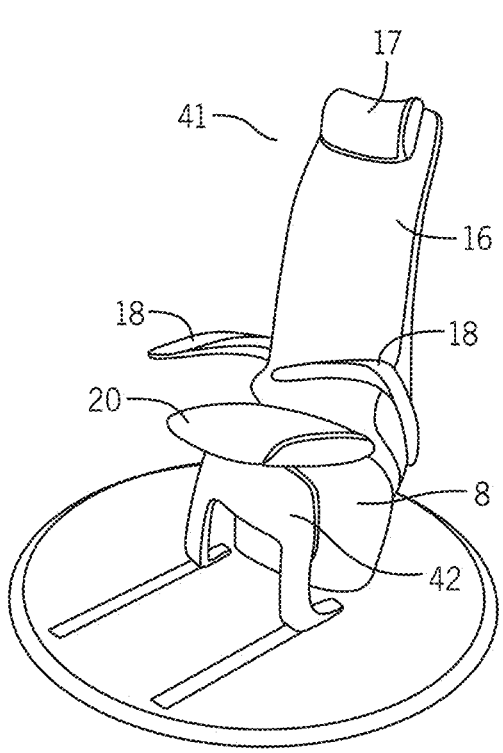
FIG. 25a illustrates a perspective view of an embodiment of a patient support assembly in a first orientation.
Figure 25B:
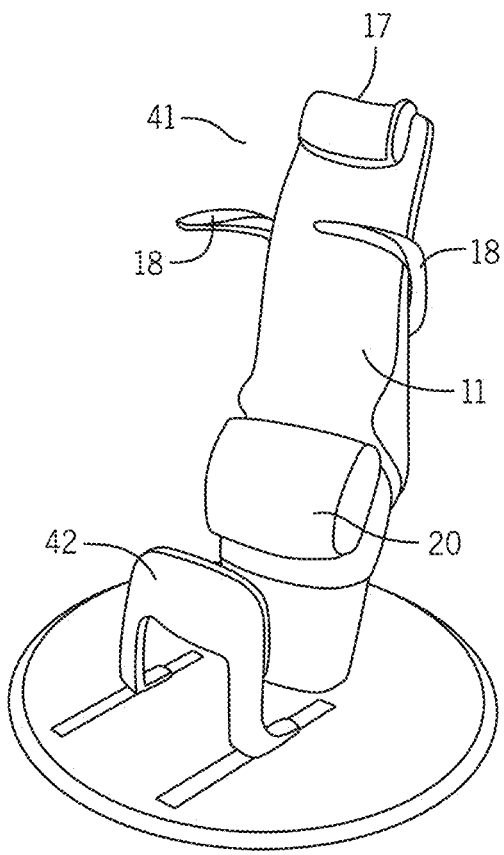
FIG. 25b illustrates a perspective view of an embodiment of a patient support assembly in a second orientation.

FIG. 25*a* and FIG. 25*b* show an embodiment of the patient support assembly 41 in a first orientation and second orientation respectively. The patient support assembly 41 may include a patient support 8 in the form of a generally elongate upright structure with an integrated back rest 16, which may be formed of some padded material and may further be contoured to conform with a patient's anatomy, for example, the curvature of a patient's back. In this manner, the patient support assembly 41 may comprise a patient support 8 and patient restraint system 15 that are integrated, rather than distinct and/or separable. The back rest 16 is adapted to sustain a back of the patient at an angle relative to the vertical axis. A patient-receiving side of the back rest 16 may be angled posteriorly to the vertical axis, so as to face the vertical axis. The back rest 16 may be vertically adjustable to receive a patient's back in either the first orientation or the second orientation. In the depicted embodiment, the back rest 16 is configured to slide along the same slanted axis as the back rest 16 in order to adjust the vertical position of the back rest 16. In an embodiment, the back rest 16 may be vertically adjustable by about 400 mm between the first orientation and the second orientation in order to accommodate patients with a height between that of a $95^{th}$ percentile American male and a $5^{th}$ percentile American female. The patient support assembly 41 may be mounted to a rotatable structure such as a rotatable disc 6 facilitating rotation of the patient support assembly 41 about a vertical axis.

A vertical location of the back rest 16 may be adjustable independently of a vertical translation of the patient 9. The vertical translation of the patient 9 may be effected by the translatable member 2, or by a vertical translation of the patient support assembly 41 relative to the translatable member 2 (for example, the patient support assembly 41 may be moveably mounted to the translatable member 2, such that the patient support assembly 41 is adapted to rotate and/or to move in a vertical direction, relative to the translatable member 2). In this way, vertical translation of the patient 9 may only adjust a vertical location of the patient 9, without affecting the patient's 9 position on the patient support assembly 41. Adjusting the vertical location of the back rest 16 may affect the patient's 9 position and cause unwanted movement, such as by changing an extent of the patient's 9 legs, and thus cause movement of the patient's 9 organs. Furthermore, when a treatment or imaging beam needs to impinge on the patient 9 in a helical pattern, the patient 9 should be vertically translated and rotated during treatment or imaging, while the patient's 9 position on the patient support assembly 41 remains constant or unchanged. Therefore, in some situations, it may be necessary to independently adjust the patient's 9 position and vertical location. A first actuator, or a first set of actuators, may be provided to adjust the patient's 9 position by adjusting a vertical location of the back rest 16. Such movement may be effectuated while the radiation source is off, in order to suit the patient's 9 position to a treatment or imaging, or in order to improve the patient's comfort. A second actuator, or a second set of actuators, may be provided to adjust the patient's 9 vertical location, for example, for translating the patient 9 while the radiation source is on, or for moving the patient 9 to align with the treatment or imaging plan, or isocentre, or beam line. The first and second actuators, or set of actuators, may operate simultaneously in order to facilitate ingress or egress of patient 9 from the patient positioning assembly 41. Other elements of the patient positioning assembly 41 may also be adjustable independently of a vertical translation of the patient 9. For example, a third actuator, or a third set of actuators, may be provided for adjusting a tilt, orientation, or vertical location of the seat member 20. Adjustment of the seat member 20 may be used to assist in positioning a non-ambulatory patient 9 from a wheelchair into the patient positioning assembly 41. Adjustment of the seat member 20 may also aid in adjusting the vertical location of the patient 9.

The shin rest 42 may be adjustably mounted to the rotatable disc 6 so as to position between the first orientation and the second orientation. The shin rest 42 may comprise a padded member in a generally vertical alignment for receiving the shins of a patient 9, and may be adjustably mounted to the rotating disc 6 to effect its position relative to the back rest 16. In the first orientation of FIG. 25*a*, the position of the shin rest 42 may be adjusted to locate underneath the seat member 20 so as not to contact with a seated patient 9 supported by the patient support assembly 41. In the second orientation of FIG. 25*b*, the shin rest may 42 be configured to locate forward of the back rest 16 to offer support to a patient's shins when that patient's back locates against the back rest 16. Alternatively, the shin rest 42 may be adjustable to locate against the shins of patient 9, and thus support patient's 9 shins, in both the first orientation and the second orientation. The shin rest 42 may be slidably mounted with respect to the rotating disc 6, and may be lockable in position. The shin rest 42 may further stabilise patient 9, by providing a supporting surface for bracing the patient against a centrifugal force that patient 9 may experience during rotation of patient support assembly 41.

Patient support assembly 41 may further include a foot rest for sustaining the feet of patient 9 in the second orientation. The foot rest may further sustain the feet of patient 9 in both first and second orientations of patient support assembly 41. In FIGS. 24 to 29, rotating disc 6, onto which patient support assembly 41 is mounted, is also the foot rest. In other examples, a foot rest that is separate of rotating disc 6, such as a raised foot rest, may be provided.

Therefore, patient support assembly 41 includes at least three main points of contact to patient 9; in the first orientation, the three main points of contact are the foot rest (i.e. rotating disc 6), the seat member 20, and the back rest 16; in the second orientation, the three main points of contact are the foot rest (i.e. rotating disc 6), the shin rest 42, and the back rest 16. The at least three points of contact may improve patient comfort by supporting or sustaining the patient 9 in three different regions of the patient's 9 body, thus allowing the patient 9 to maintain their position for longer, uninterrupted periods, whilst preventing patient 9 from sliding out of position, particularly when in the second orientation. The at least three points of contact further improve patient stability by reducing patient movement, compared to configurations with fewer than three points of contact. Fewer than three points of contact might require patient 9 to exert a force in order to maintain their position, particularly when in the second orientation. The reproducibility of patient's 9 position may also be improved by providing at least three points of contact.

The seat member 20 may attach with the patient support assembly 41 by a pivotal mount. By this arrangement, the seat member 20 may be positioned to depend outwardly from the back rest 16 when the patient support assembly 41 is in a first orientation to thereby offer support for a seated patient's buttocks when that patient's back is located against the back rest 16. Also by this arrangement, the seat member 20 may be positioned downward about the pivot to locate toward the same plane as the back rest 16 to locate away from a patient 9 received by the patient support assembly 41 in a second position as shown in FIG. 25*a*.

The arm rests 18 may be adjustably mounted to the patient support assembly 41 to affect their position relative to the back rest 16 so as to accommodate patients of differing size. The adjustability of the arm rests 18 may also facilitate the patient's arms being supported in various positions to allow a radiation 11 source to target the correct part of the patient's anatomy. For example, positioning the arm rests 18 at a high vertical location relative to the back rest 16 may allow the arm rests 18 to receive the patients arms above the level of the chest, and may also aid in facilitating the patient 9 remaining still by offering comfortable support. The arm rests 18 may support the weight of the upper arms of patient 9, and they may aid in maintaining and reproducing a specific positional arrangement of patient's 9 upper body. The arm rests 18 may further stabilise patient 9 during rotation, or any other movement, of patient support assembly 41. In addition, the arm rests 18 may be adapted for mounting, connecting, or affixing measurement instruments thereto, such as quality assurance equipment, or any other instrument relevant to the therapeutical or imaging use of patient positioning assembly 1. For example, quality assurance equipment may be mounted to arm rests 18 and positioned at a mechanical isocentre of patient positioning assembly 1 for conducting tests such as measuring the output of the radiation source and the alignment of the radiation beam relative to the axis of rotation of patient support assembly 41. Accordingly, arm rests 18 may include one or more brackets, attachments, or other mounting mechanisms for mounting measurement instruments thereto.

Figures 26A, 26B:
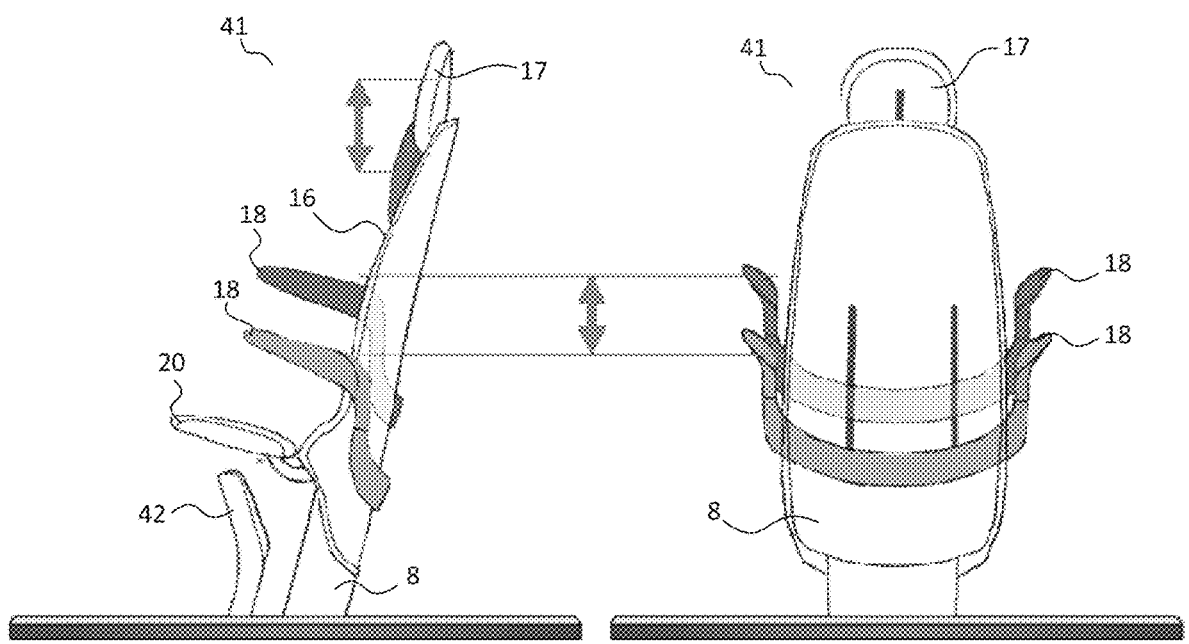
FIG. 26a illustrates a side view of an embodiment of a patient support assembly in a first orientation.
FIG. 26b illustrates a rear view of an embodiment of a patient support assembly in a first orientation.

FIGS. 26*a* and 26*b* show an embodiment of the patient support assembly 41 in the first orientation, or first configuration, in profile and rear view respectively. In addition to the adjustable arm rests 18 as hereinbefore described, the patient positioning assembly 41 may further include a head rest 17 that is vertically adjustable in position to accommodate patients of varying size. In an embodiment, the head rest 17 may be slidably connected with the back rest 16 to effect the vertical position of the head rest 17 relative thereto so as to comfortably receive patients of varying size. The patient positioning assembly 41 in the first orientation may be suitable for targeting the head, neck, breast and/or lungs of a patient with a radiation source.

Figures 27A, 27B:
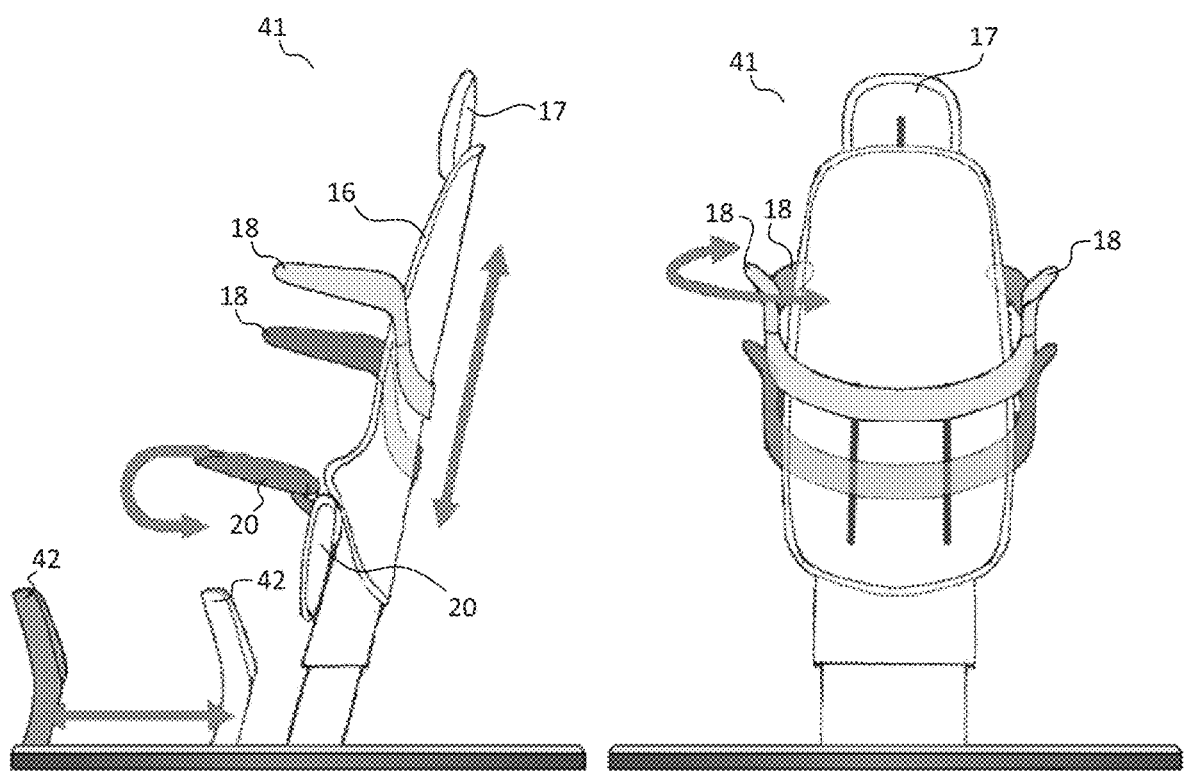
FIG. 27a illustrates a side view of an embodiment of a patient support assembly in a second orientation.
FIG. 27b illustrates a rear view of an embodiment of a patient support assembly in a second orientation.

FIGS. 27*a* and 27*b* show an embodiment of the patient support assembly 41 in the second orientation, or second configuration, in profile and rear view respectively. In the second orientation, the seat member 20 has been folded downwardly about its pivotable connection toward alignment with the plane of the back rest 16, the back rest 16 has been adjusted vertically upwards along the slanted axis of the back rest 16, the shin rest 42 has been adjusted horizontally away from the back rest 16 and the arm rests 18 have been adjusted vertically with respect to the back rest 16. FIG. 45*b* further shows that the arm rests 18 may swivel to locate in various positions in a generally transverse patient axis to comfortably accommodate the patient in a variety of treatment positions.

FIGS. 28*a*, 28*b* and 28*c* show a patient positioning assembly 1 using the patient support assembly 41 adapted to receive a patient with a posteriorly angled torso. Such an embodiment may be contained within a bunker of ceiling height 2600 mm in order to treat a 95$^{th}$ percentile American patient being targetable between the head and the thighs with a central axis of a fixed treatment 11 beam source positioned at a height of about 1480 mm. The clearance bore about which the patient may be translated and rotated may be about 1100 mm in diameter, and the vertical translation of the translatable member 2 may be about 650 mm.

Figure 29:
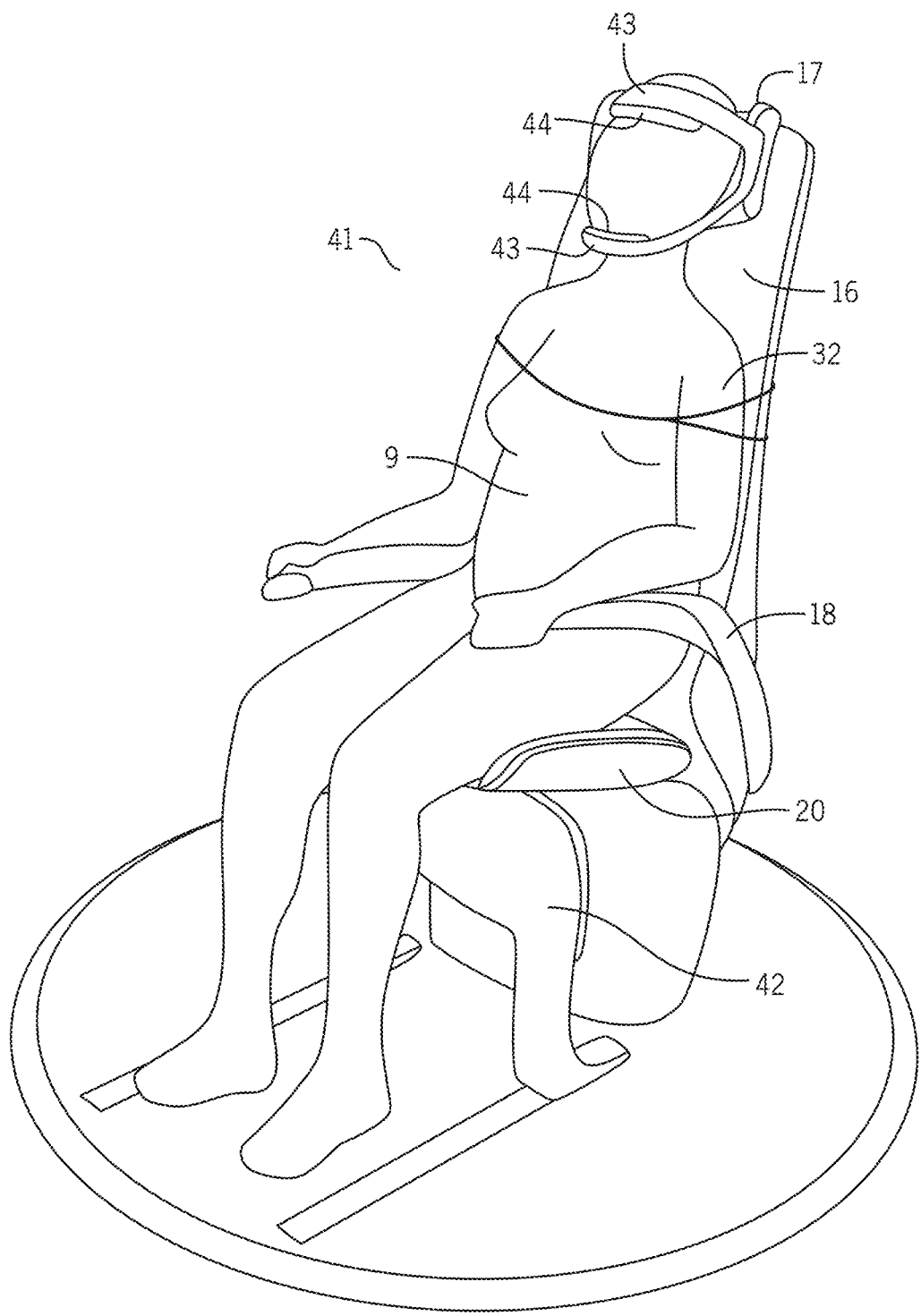
FIG. 29 illustrates a perspective view of an embodiment of a patient support assembly.

The patient positioning assembly 41 adapted to receive a patient with a torso angled posteriorly with respect to the vertical axis and having their ankles supported by a shin rest 16 in the second orientation may be advantageous in that the patient position is largely self-supporting and comfortable. Accordingly, the patient may be able to maintain the required treatment position using this assembly in a comfortable manner for appreciable lengths of time, such that the patient restraint system 15 required to immobilise the patient may be minimal. Nonetheless, in addition to the elements of the patient support assembly hereinbefore discussed in relation to this embodiment, namely, the back rest 16, shin rest 42, seat member 20, arm rests 18 and head rest 17, other elements of patient restraint systems 15 hereinbefore discussed in relation to other embodiments may also be used, including harnesses, inflatable elements, elongate straps and the like. In an embodiment, the patient support assembly 41 may include an elongate strap 32 adapted to locate across a patient's chest and optionally around a patient's shoulders as depicted in FIG. 29. In an embodiment (not depicted), the patient support assembly of FIGS. 25*a* and 25*b* may include an elongate strap 32 adapted to locate about a patient's lap when received by the assembly 41. In an embodiment, a head and neck restraint may be used to immobilise the patient's head with respect to the patient support assembly. FIG. 29 shows a patient received by a patient support assembly 41 in the first orientation with their head secured in position by an embodiment of a head and neck restraint. In this embodiment, two elongate bands 43 are used to immobilise the patient's head, both bands 43 being braced to the head rest 17, with one such band 43 located against the patient's forehead, and the other such band 43 locates about the patient's chin. This embodiment may further include a mould 44 located between the band 43 and the forehead, and a mould 44 located between the band 43 and the chin. These moulds 44 may be adapted to conform with the patient's anatomy they locate against, and may further be custom produced during simulation scanning to adapt to the specific anatomy of a particular patient 9. The moulds 44 may be formed of some resilient material such as foam, and the bands 43 may be formed of some suitable material such as a rigid plastic.

Referring to FIGS. 30 to 41, there is illustrated another example embodiment of a patient support assembly 41 that may be suitable for use with embodiments of the patient positioning assembly 1 described herein. The patient support assembly 41 is configurable between a first configuration or orientation, in which a patient is sustained in a seated position, and a second configuration or orientation, in which the patient is sustained in a standing, or a substantially standing position (e.g. a generally standing, or semi-upright standing position).

Figure 30:
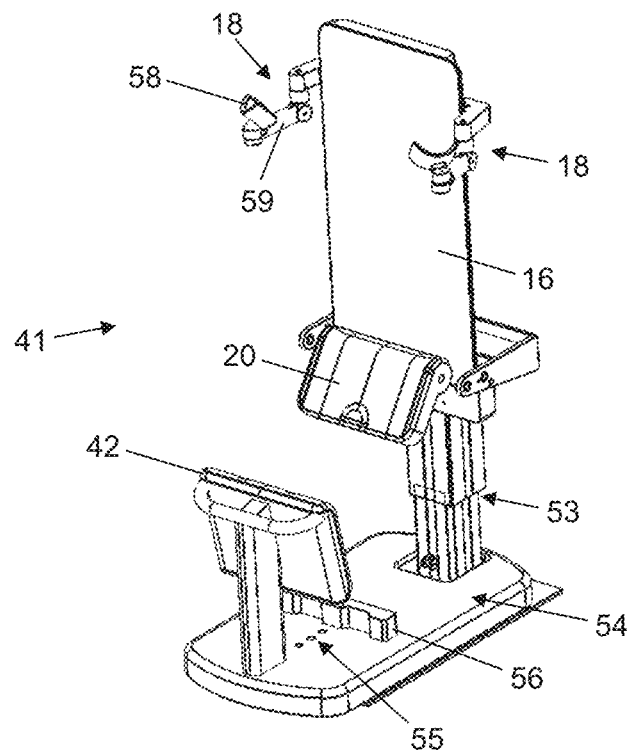
FIG. 30 illustrates a perspective view of another example embodiment of a patient support assembly.
Figure 31:
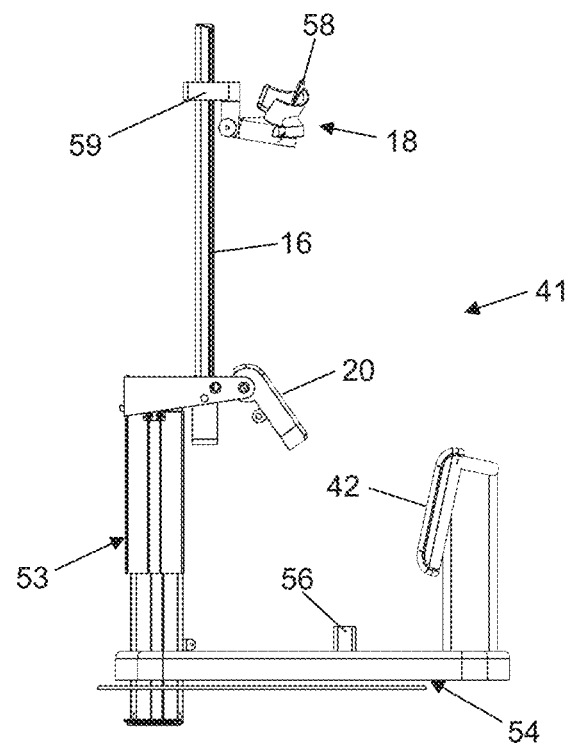
FIG. 31 illustrates a side view of the patient support assembly of FIG. 30.

Referring to FIGS. 30 and 31, the patient support assembly 41 comprises a back rest 16 for sustaining or supporting a back of the patient. The back rest 16 is mounted to a pillar or post 53 supporting the back rest 16. The pillar 53 is itself mounted to a platform, base, or surface 54. The patient support assembly 41 further comprises a seat member 20 for sustaining or supporting a posterior, buttocks, or thighs of the patient. The seat member 20 is mounted to the pillar 53 in close proximity to the back rest 16. In other examples, the seat member 20 may be mounted to the back rest 16. The back rest 16 and the seat member 20 are pivotally mounted to the pillar 53 for adjusting their respective inclinations. Furthermore, vertical height of the pillar 53 is adjustable for adjusting the vertical height of the back rest 16 and seat member 20. The patient support assembly 41 further comprises a shin rest 42 for sustaining or supporting shins of the patient (i.e. a front part of the patient's legs, between the knees and the ankles). The shin rest 42 is mounted to the platform 54 in front of the back rest 16 and the seat member 20. The shin rest 42 is offset from the back rest 16 such that it faces the shins of the patient when the patient has their back positioned against the back rest 16. The platform 54 comprises a plurality of holes 55 for receiving an apposite mating member of the shin rest's 42 mounting base. The holes 55 are provided at several horizontal offsets relative to the back rest 16, such that the horizontal distance between the back rest 16 and the shin rest 42 may be adjusted by mounting the shin rest 42 to a different hole 55. In other embodiments, other arrangements or mechanisms may be provided for adjusting a horizontal distance between the shin rest 42 and the back rest 16, such as a rail along which the shin rest 42 may be moved, and corresponding locking arrangements for fixing the shin rest 42 at a given location. The back rest 16, the seat member 20, and the shin rest 42 comprise substantially flat surfaces, and may further comprise padding for accommodating a respective area of the patient's body. The patient support assembly 41 further comprises a pair of foot braces 56 for securing feet of the patient. The foot braces 56 are mounted to the platform 54 between the back rest 16 and the shin rest 42. The foot braces 56 may comprise straps, clasps, or other arching pieces adapted to fasten over a top side of the patient's feet for securing them to the platform 54. In other examples, means other than foot braces 56 may be provided for securing the patient's feet to the platform 54, such as foot-shaped indentations, or raised foot stops.

The patient support assembly 41 further comprises arm rests or arm supports 18 for sustaining arms of the patient. Arm rests 18 are mounted to the back rest 16 at a left and right side of the back rest 16 to receive respective left and right arms of the patient. The vertical height of the arm rests 18, as well as their location relative to the back rest 16, may be adjusted for accommodating patients of different sizes and different patient positions. Each arm rest 18 comprises a bent portion 58 for receiving a portion of the upper arm of the patient extending between the shoulder and the elbow. The bent portion 58 is pivotally mounted to arm 59, which is connected to the back rest 16, for orientating the bent portion 58 to suit the patient's physical dimensions. The arm rests 18 may sustain the arms of the patient in a predetermined position, such as an overhead position as shown, or a downwards, lateral position such that the arms are positioned at respective left and right sides of the patient.

The arm rests 18 may be adapted for mounting, connecting, or affixing measurement instruments thereto, such as quality assurance equipment, or any other instrument relevant to the therapeutical or imaging use of the patient support assembly 41.

Figure 32:
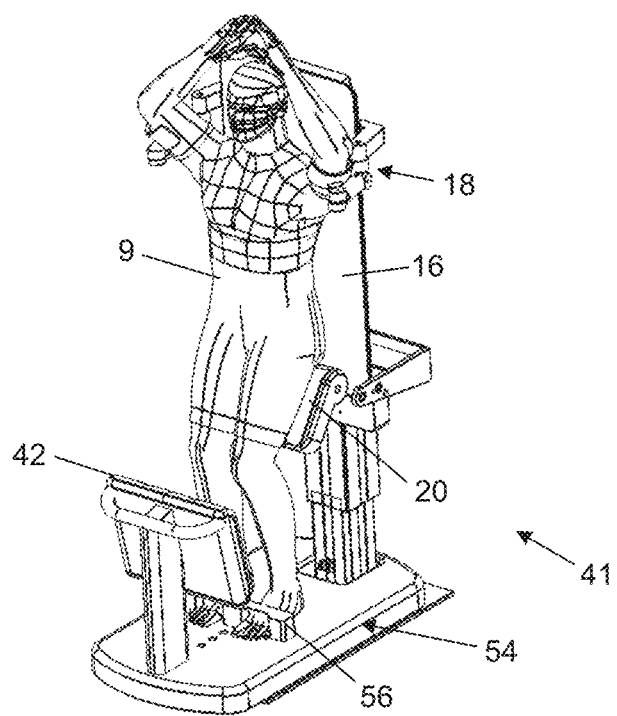
FIG. 32 illustrates a perspective view of the patient support assembly of FIG. 30, in a second orientation.
Figure 33:
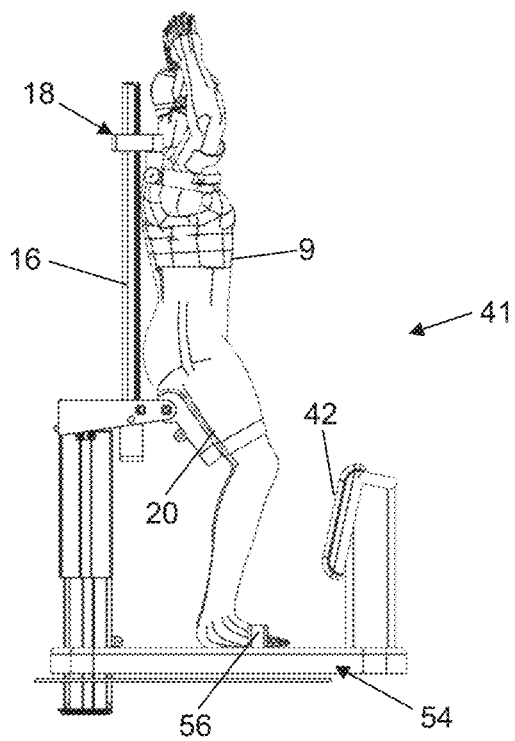
FIG. 33 illustrates a side view of the patient support assembly of FIG. 30, in a second orientation.

Referring to FIGS. 32 and 33, there is illustrated the patient support assembly 41 in the second configuration, and a patient 9 located in the patient support assembly 41 in a substantially standing position. Arm rests 18 engage the patient's 9 upper arms and sustain their arms in an overhead position, with the patient's 9 arms being angled vertically upwards and extending above a head of the patient.

It may not be necessary for each component of the patient support assembly 41 (i.e. the back rest 16, the seat member 20, the shin rest 42, the foot braces 56, and the arm rests 18) to sustain or support the patient in either the first or second configuration. Preferably, though not necessarily, the patient support assembly sustains the patient at three or more different points along the patient's body. The at least three supported regions of the patient may be end points of the patient (e.g. the patient's feet) or regions near moveable joints of the patient (e.g. knees, shoulders, hips). In this way, the patient support assembly 41 may aid the patient 9 in maintaining a predetermined position.

Figure 34:
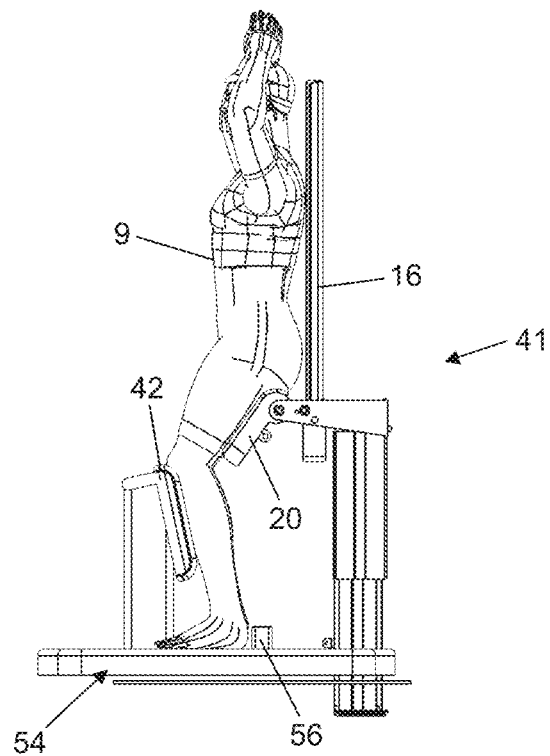
FIG. 34 illustrates a side view of the patient support assembly of FIG. 30, in another second orientation.
Figure 35:
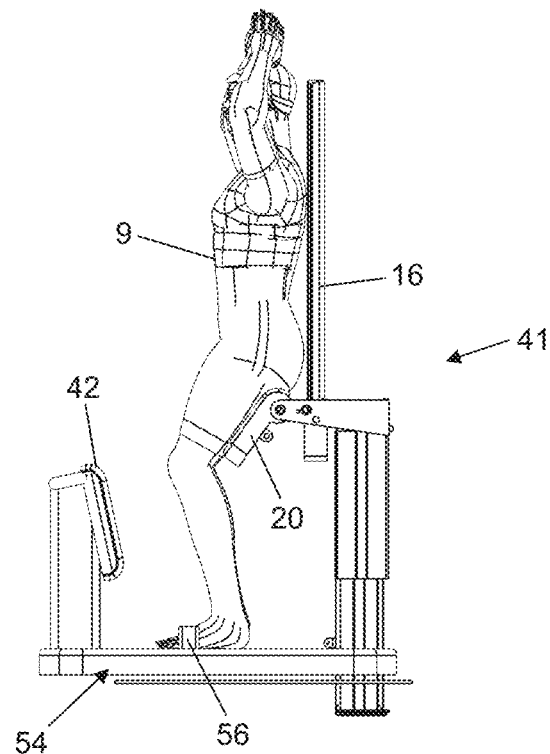
FIG. 35 illustrates a side view of the patient support assembly of FIG. 30, in another second orientation.

Referring to FIGS. 34 and 35, there are illustrated two examples of second configurations of the patient support assembly 41 for sustaining the patient 9 in a substantially standing position, with the patient's thighs at least partly extending along a vertical direction, and the patient's knees being bent relative to the thighs. In the example illustrated in FIG. 34, the patient's 9 back is sustained by back rest 16, the patient's 9 posterior is sustained by seat member 20, and the patient's 9 shins are sustained by the shin rest 42. The patient's 9 feet however are not secured by foot braces 56, which are positioned behind the patient's 9 ankles. In contrast, in the example illustrated in FIG. 35, the patient's 9 feet are secured by foot braces 56, while the patient's 9 shins are not sustained by the shin rest 42, which is moved apart from the patient's 9 shins. The patient's 9 arms may be sustained in an overhead position by the arm rests 18 (not shown). Alternatively, the patient's 9 arms may be positioned so as to extend downwardly along the patient's 9 sides.

Figure 36:
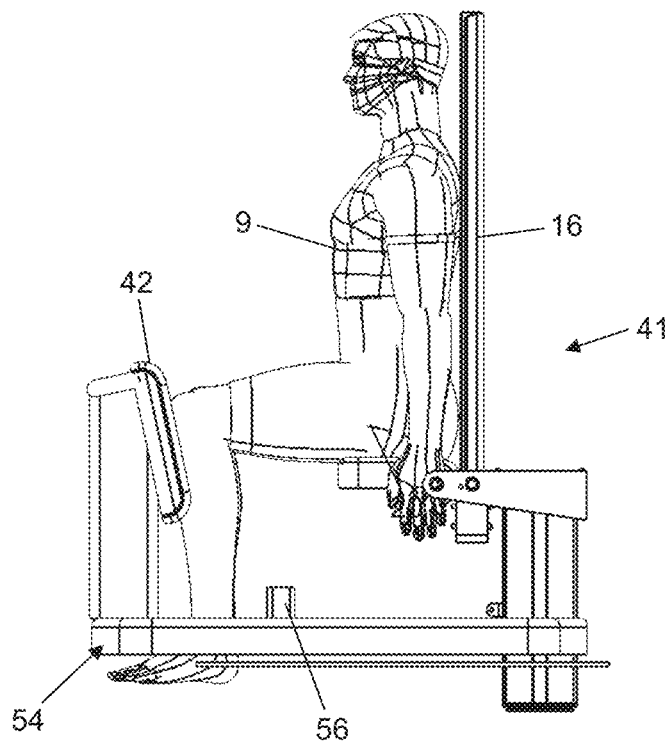
FIG. 36 illustrates a side view of the patient support assembly of FIG. 30, in a first orientation.

Referring to FIG. 36, there is illustrated an example of a first configuration of the patient support assembly 41 for sustaining the patient 9 in a seated position, with the patient's 9 thighs extending along a substantially horizontal direction, and the patient's 9 knees being bent approximately perpendicularly relative to the thighs. The patient's 9 back is sustained by back rest 16, the patient's 9 posterior is sustained by seat member 20, and the patient's 9 shins are sustained by the shin rest 42, thus preventing the patient 9 from sliding forwards along seat member 20. In the example illustrated in FIG. 36, the patient's 9 feet are not secured by foot braces 56, which are positioned behind the patient's 9 ankles. In other examples, the patient's 9 feet may be secured by foot braces 56, and the shin rest 42 may be moved apart from the patient's 9 shins. The patient's 9 arms are positioned so as to extend downwardly along the patient's 9 sides. In other examples, the patient's 9 arms may be sustained in an overhead position by the arm rests 18 (not shown).

The patient support assembly 41 may be mounted to a rotatable structure such as the rotating disc 6 of the translatable member 2, described herein, for facilitating rotation of the patient support assembly 41 about a vertical axis. For example, platform 54 may be mounted to the rotating disc 6. In other examples, platform 54 is integrally formed with the rotating disc 6 and forms part of the rotating disc 6.

Referring to FIGS. 37 to 41, there is illustrated the patient support assembly 41 adapted to move or translate along a vertical direction. The patient support assembly 41 is mounted to and above a scissor-lift mechanism 60. A fixed end 61 of the scissor-lift mechanism 60 may connect to a surface, such as the rotating disc 6 of the translatable member 2, while a moveable end 62 of the scissor-lift mechanism 60 engages the platform 54 for translating the patient support assembly 41 relative to fixed end 61. In other example embodiments, any lifting mechanism other than a scissor-lift mechanism, such as a pulley lift system, a counterweight system, or a hydraulic lift, may be provided for adjusting a vertical location of the patient support assembly 41. In this way, a vertical location of the patient support assembly 41, and of the patient 9, may be adjusted without affecting the configuration of the patient support assembly 41 or the position of the patient 9. The patient support assembly 41 and the translatable member 2 may share the same vertical axis. In this arrangement, therefore, the patient support assembly 41 and the translatable member 2 may be adapted to independently move along the same vertical axis.

Figure 37:
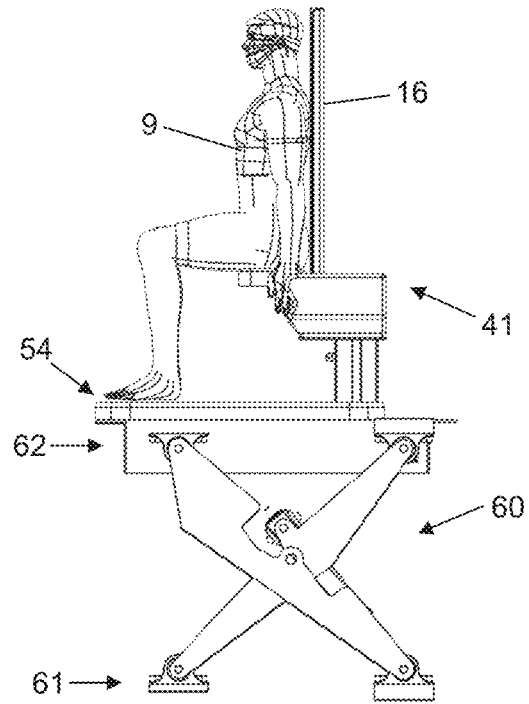
FIG. 37 illustrates a side view of the patient support assembly of FIG. 30, in a first orientation, mounted to a lifting mechanism.
Figure 38:
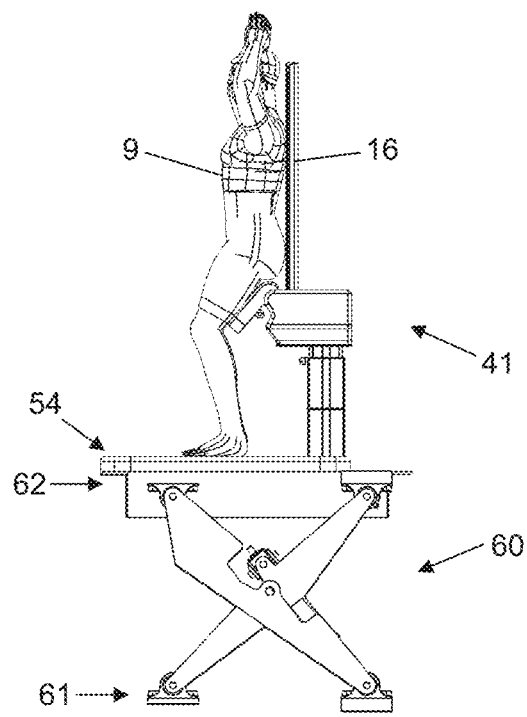
FIG. 38 illustrates a side view of the patient support assembly of FIG. 37, in a second orientation, with a back rest aligned to a vertical axis.
Figure 39:
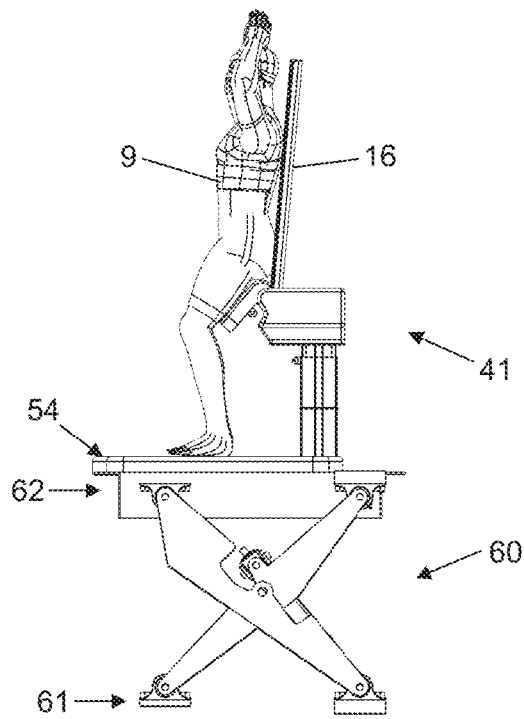
FIG. 39 illustrates a side view of the patient support assembly of FIG. 37, in a second orientation, with a back rest inclined posteriorly relative to a vertical axis.
Figure 40:
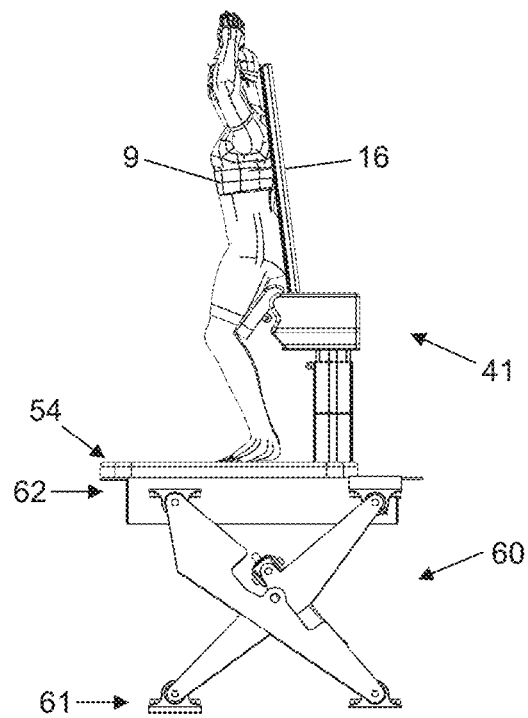
Figure 41:
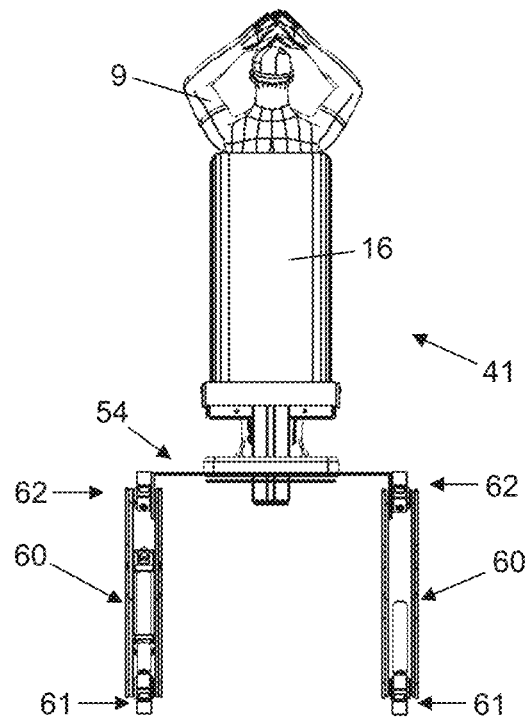
FIG. 41 illustrates a rear view of the patient support assembly of FIG. 38.

FIGS. 37 to 40 also illustrate the adjustability of the inclination of the back rest 16. FIGS. 37 and 38, which illustrate the patient support assembly in the first and second configuration, respectively, further illustrate a plane of the back rest 16 being parallel to a vertical axis of the patient support assembly 41, such that a torso of the patient 9 is also substantially vertically oriented. In FIG. 39, the plane of the back rest 16 is tilted clockwise relative to the vertical axis. The back rest 16 is therefore inclined posteriorly to the vertical axis, such that the patient's 9 torso is tilted posteriorly relative to the vertical axis. In FIG. 40, the plane of the back rest 16 is tilted counter-clockwise relative to the vertical axis. The back rest 16 is therefore inclined anteriorly to the vertical axis, such that the patient's 9 torso is tilted anteriorly relative to the vertical axis.

In some examples, the patient support assembly 41 is adapted to tilt or pivot relative to a horizontal plane of the translatable member 2, or any other fixed horizontal surface. The platform 54 may be pivotally mounted to the translatable member 2 such that the patient support assembly 41 may be tilted, or pivoted, about a point of the platform 54. The point of tilting may be a centre point of the platform 54, or any other point located within an area defined by the platform 54. For example, the platform 54 may be mounted onto a rounded member, which may be in the shape of a sphere, a hemisphere, a portion of a sphere, or other rounded surface, such that the platform 54 is able to tilt and rotate relative to the rounded member. Pivoting of the platform 54 about the rounded member may provide two degrees of freedom in the pitch and roll of the platform 54 relative to the rounded member. This freedom of movement may be used for tilting the patient support assembly 41 (and the patient 9), for example, for adjusting the angular position of the patient 9 for alignment to a treatment or imaging plan, or for avoiding irradiating areas of the patient 9 not intended for radiation treatment or imaging. The mounting of the platform 54 to a rounded member, such as a ball joint, or other rounded joint, gives a fixed point of reference in space around which the angular movements are orientated. Actuators may be provided for controlling the orientation and magnitude of tilt of the base relative to the rounded member in order to improve stability of the base.

Figure 42:
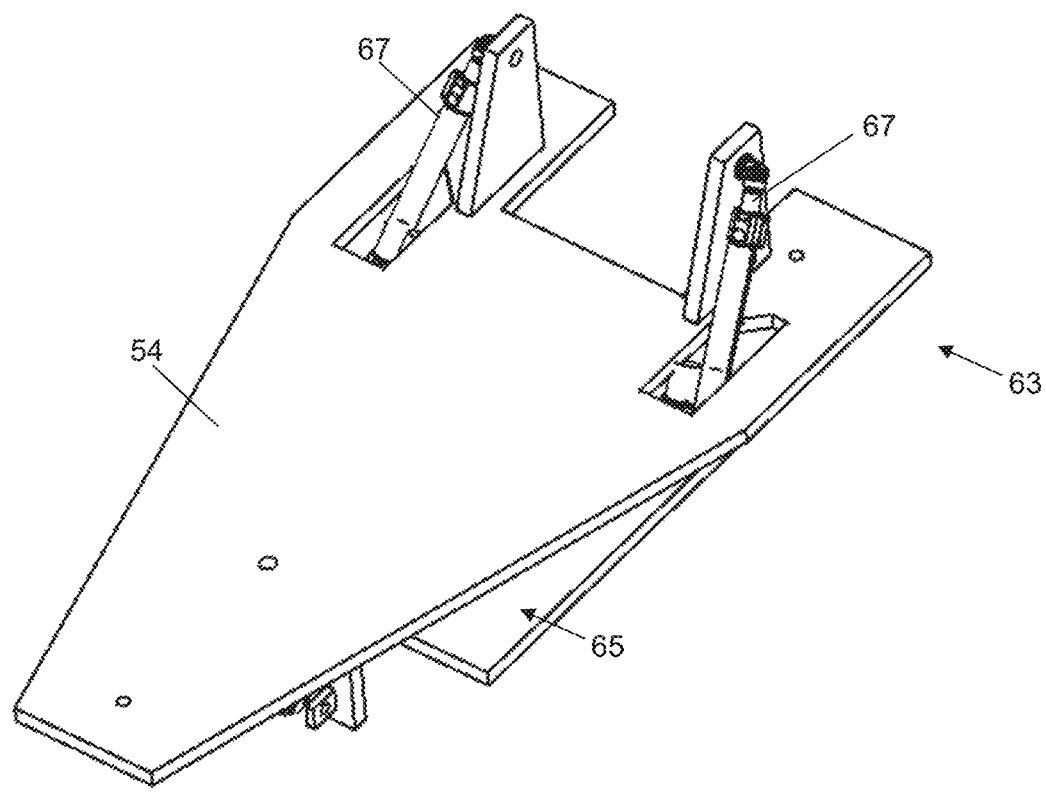
FIG. 42 illustrates a perspective view of an example embodiment of a pivotable base for supporting a patient support assembly.
Figure 43:
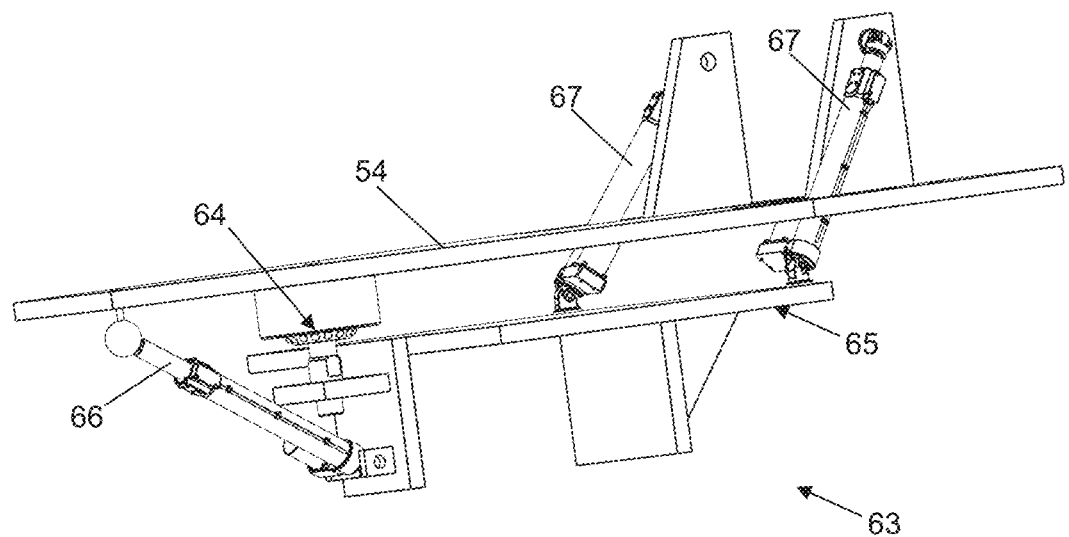
FIG. 43 illustrates a side view of the pivotable base of FIG. 42.

Referring to FIGS. 42 and 43, there is illustrated a pivotable base 63 for the patient support assembly 41. The pivotable base 63 comprises a platform 54, onto which the patient support assembly 41 is mounted. The platform 54 is pivotally connected by a spherical joint 64 to a stand 65. The stand 65 may be attached to a fixed surface, or to the rotating disc 6 of the translatable member 2. The pivotable base 63 further comprises three actuators connected between platform 54 and stand 65, for pivoting the platform 54 about spherical joint 64, relative to the stand 65. The three actuators comprise one front actuator 66 located in proximity to the spherical joint 64 and engaging a first side of the platform 54, and two rear actuators 67 located distally to the spherical joint 64 and engaging a second side of the platform 54, opposite the first side. In some examples, such as during a pitch movement of the platform 54, the front actuator 66 may be in a push-pull arrangement with the rear actuators 67 (i.e. when the rear actuators 67 expand, the front actuator 66 contracts, and vice versa). In other examples, such as during a roll movement of the platform 54, the rear actuators 67 may be in a push-pull arrangement with each other without significant movement in the front actuator 66. The spherical joint 64 (and thus, the pivot point of the pivotable base 63) is located offset from a geometrical centre of the platform 54. In some examples, the pivot point of the pivotable base 63 may be displaced, or offset, from the centre of the base and from the isocentre of the treatment or imaging system. In some examples, any number of actuators may be provided. By arranging the actuators in a triangular configuration, with the pivot point located in proximity to one of the actuators, yaw movement arising from a combination of pitch and roll may be reduced, compared to a situation where the pivot point is equidistant from all the actuators. In some examples, the arrangement of the pivot point and the actuators is such that the majority of the load of the patient support assembly 41 and the patient 9 is located between the spherical joint 64 and the rear actuators 67.

Figure 44:
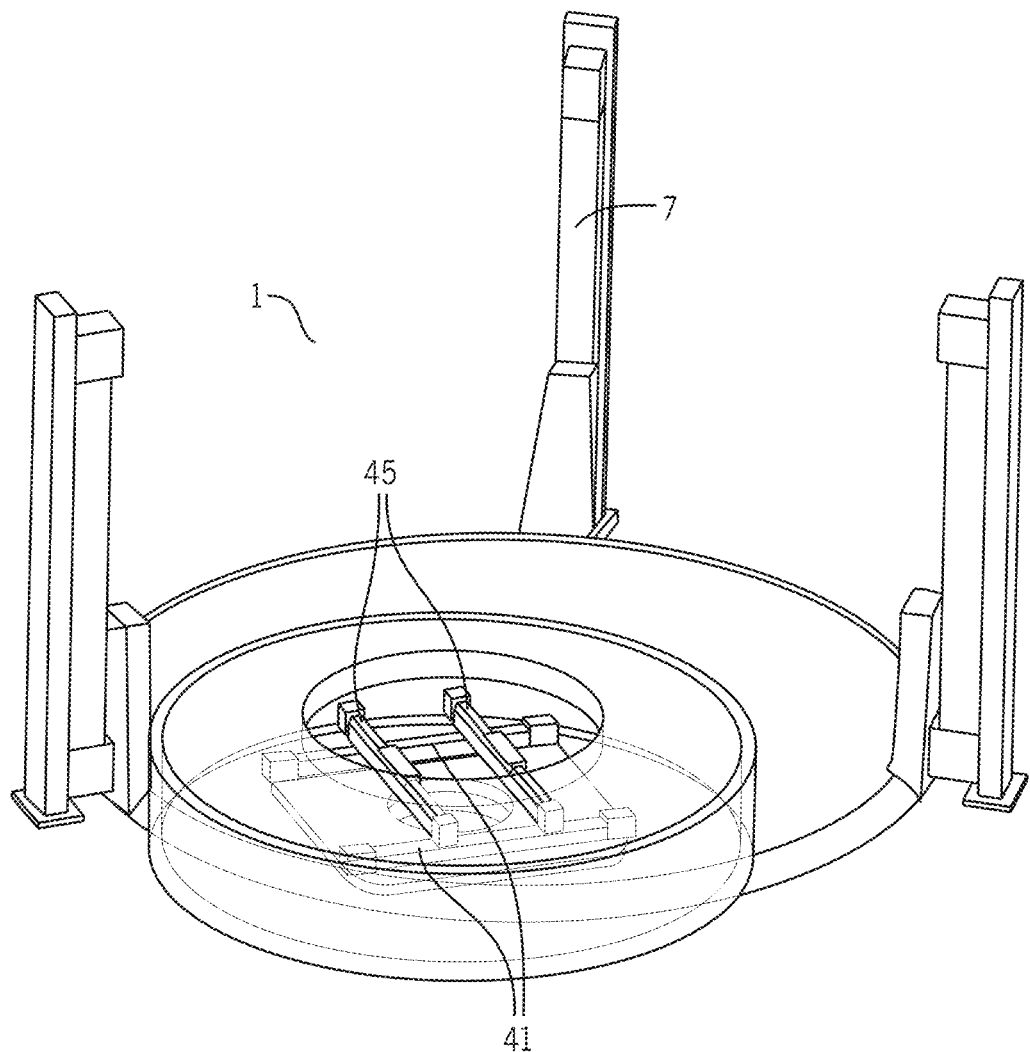
FIG. 44 illustrates a partial view of a patient positioning assembly showing an assembly to effect the horizontal position of a patient support assembly.

In addition to being rotatable about a vertical axis, the patient support assembly may be translatable in a horizontal plane. FIG. 44 shows an embodiment of an arrangement for translating the patient support assembly in a horizontal plane orthogonal to the vertical axis of rotation. This arrangement may include two pairs of parallel rails 45, 46 in orthogonal relation, the patient support assembly being slidably connected to a first pair of rails 46 for translation in a first orthogonal direction, and the first set of rails 45 being slidably connected to a second pair 46 of rails for translation in a second orthogonal direction.

The patient positioning assembly 1 as herein described may offer certain advantages over similar devices known to the art. Rotating a patient 9 about a vertical axis may involve less deformation of a patient's 9 internal anatomy as opposed to rotating a patient 9 about a horizontal axis, thus simplifying the targeting of a patient 9 by a fixed treatment beam or an adjustable treatment beam. The vertical upright position of the patient 9 may also be more comfortable than a horizontal position, particularly when a patient 9 is undergoing treatment for a long period of time. Furthermore, the upright orientation and vertical translation of the patient 9 may involve a decreased equipment footprint, whilst the fixed treatment beam or a vertically adjustable treatment beam may result in simplified shielding requirements compared with arrangements that involve a moving treatment beam that rotates with respect to a stationary patient.

In certain embodiments, the decreased equipment footprint and simplified shielding requirements may facilitate the patient positioning assembly being located in a train carriage or a bus thereby making the delivery of medical care by the patient support assembly accessible for remote locations.

Figure 45:
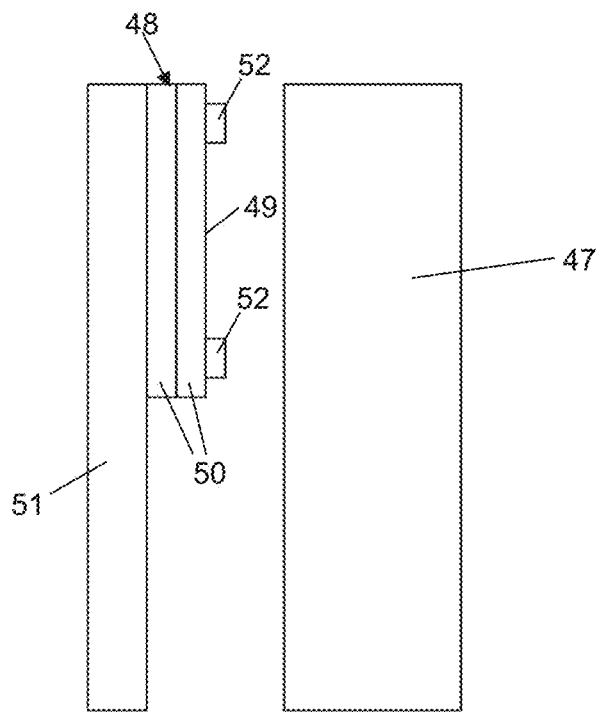
FIG. 45 illustrates a side view of an embodiment of an assembly for absorbing a radiation beam.
Figure 46:
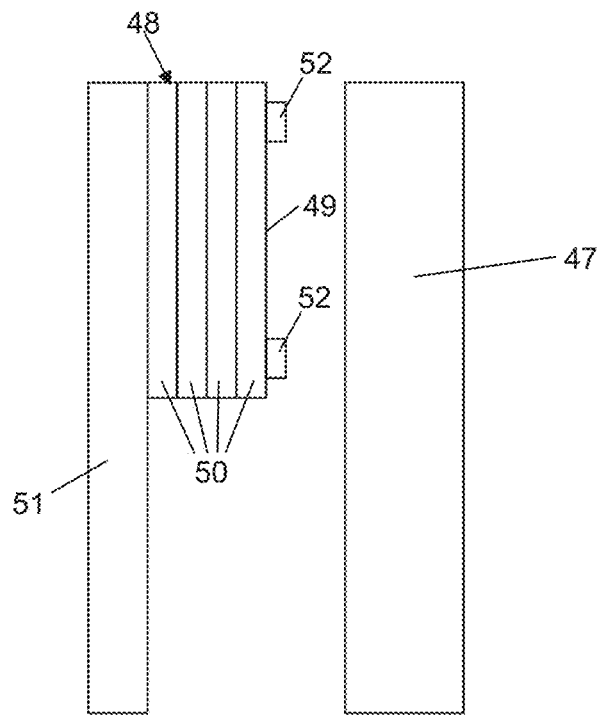
FIG. 46 illustrates a side view of another embodiment of an assembly for absorbing a radiation beam.
Figure 47:
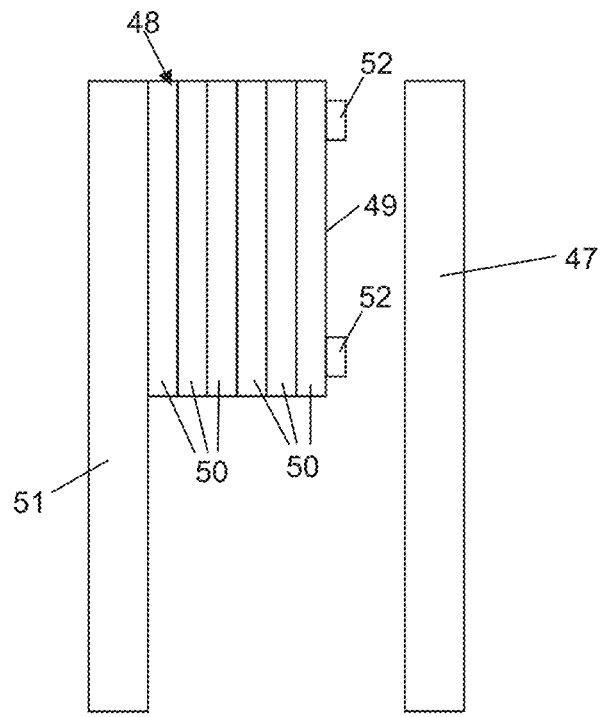
FIG. 47 illustrates a side view of another embodiment of an assembly for absorbing a radiation beam.

Referring to FIGS. 45 to 47, there is illustrated an assembly for absorbing a radiation beam outputted by a radiation source. The assembly includes wall 47 defining a space, area, or region in which the patient positioning assembly 1 (including the radiation source) is located. The wall 47 may be a wall, or a section of a wall, of a bunker or other structure that encloses or partially encloses the patient positioning system 1. The wall 47 is adapted to intersect a path of the radiation beam during use of the patient positioning assembly 1, for example, for radiation treatment or radiation imaging. Therefore, the wall 47 may extend opposite an output port of the radiation source, but be located behind the patient 9, relative to the radiation source, such that the patient 9 is interposed between the radiation source and the wall 47. The assembly further includes a beam-stopper shield 48 located on an opposite side of the wall 47 relative to the patient positioning assembly 1. The beam-stopper shield 48 has an absorption area 49 facing the radiation beam for absorbing the radiation beam. The absorption area 49 may have a size, or dimensions, approximately equivalent to a maximum range of scattering, or spread, of the radiation beam.

The beam-stopper shield 48 may include multiple absorption layers 50 for absorbing the radiation beam, where the absorption layers 50 may be stacked, or piled, over one another. The absorption layers 50 may be held together by securing bolts which traverse the whole length of the stack of absorption layers 50 and connect to a column 51, which supports the beam-stopper shield 48. Plates 52, or nuts, may attach to the bolts over the outermost absorption layer 50 to fasten the stack of absorption layers 50 together. The wall 47 may also be adapted to at least partially absorb the radiation beam, with the number of absorption layers 50 varying based at least partly on the thickness of the wall 47. Therefore, referring to FIG. 45, the wall 47, having a first thickness, acts as the primary radiation shield and only two absorption layers 50 are used for absorbing residual radiation power that travels through the wall 47. Referring to FIG. 46, the wall 47 has a second thickness that is lower than the first thickness. Here the beam-stopper shield 48, which includes four absorption layers 50, is the primary radiation shield, whilst wall 47 absorbs a reduced amount of radiation. Referring to FIG. 47, the wall 47 has a third thickness that is lower than the second thickness. Here the wall 47 absorbs minimal or no radiation, with the beam-stopper shield 48, which includes six absorption layers 50, operates as the principal radiation shield.

By providing a beam-stopper shield 48 which is separate from the wall 47 of the bunker, the shielding requirements of the bunker may be reduced, further reducing the size of the bunker and the bunker costs (e.g. material costs). This arrangement takes advantage of the fact that the patient positioning assembly 1 allows the radiation source to be fixed in place, such that during use it may operate at one single beam angle. Therefore, the radiation shielding may be concentrated at one location, based on the orientation of the fixed radiation source. The provision of a dedicated beam-stopper shield 48 may allow treatment or imaging to be executed in bunkers or structures that are not fully equipped with primary shielding, such as a moving structure (e.g. a train or a truck). Furthermore, the amount of radiation absorption of the beam-stopper shield 48 may be reconfigured by adjusting the number of absorption layers 50.

Figure 48:
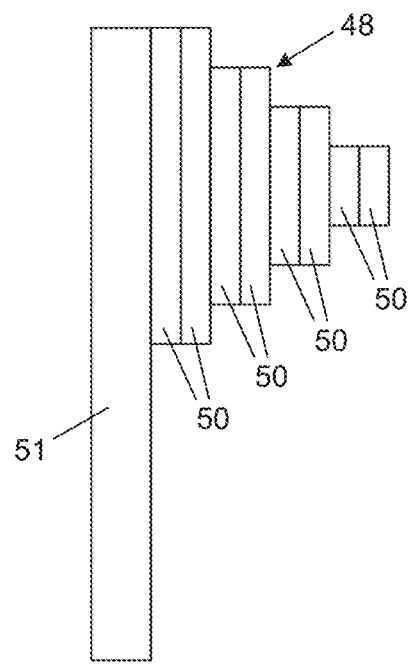
FIG. 48 illustrates a side view of an embodiment of a beam-stopper shield.
Figure 49:
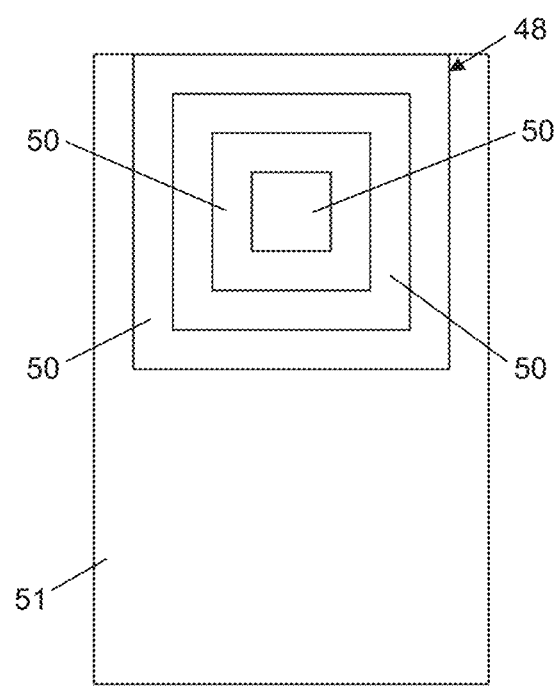
FIG. 49 illustrated a front view of the embodiment of FIG. 48.

Referring to FIGS. 48 and 49, there is illustrated an alternative embodiment of the beam-stopper shield 48, including absorption layers 50 with different absorption area 49 sizes. The absorption layers 50 are stacked in order of increasing absorption area 49, with absorption layers 50 that have smaller absorption areas 49 being located nearer to the radiation source than absorption layers 50 that have larger absorption areas 49. This arrangement may rely on the reduced confinement and intensity of the radiation beam as it travels away from the radiation source. By reducing the size of the absorption layers 50 nearer to the radiation source, the weight, material, and cost requirements of the beam-stopper shield 48 can be reduced.

Some of the embodiments hereinbefore described refer to a patient support assembly 1 configured with respect to patients 9 with height according to a $95^{th}$ percentile American man and a $5^{th}$ percentile Japanese woman. It is to be understood that this is a preferred embodiment suitable for use with a wide range of patient populations, and that patient support assemblies 1 configured to receive patients 9 of a different range of heights is equally permissible.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

In the foregoing description of preferred embodiments, specific terminology has been resorted to for the sake of clarity. However, the invention is not intended to be limited to the specific terms so selected, and it is to be understood that each specific term includes all technical equivalents which operate in a similar manner to accomplish a similar technical purpose. Terms such as "top" and "bottom", "front" and "rear", "inner" and "outer", "above", "below", "upper", "lower", "vertical", "horizontal", "upright" and the like are used as words of convenience to provide reference points and are not to be construed as limiting terms.

Many modifications will be apparent to those skilled in the art without departing from the scope of the present invention.

The invention claimed is:

1. A patient positioning assembly for orientating a patient with respect to a radiation source, wherein the patient positioning assembly comprises:
   a translatable member movable in a vertical direction between a vertically downwards first position and a vertically upwards second position; and
   a patient support assembly mounted to the translatable member and adapted to rotate relative to the translatable member about a vertical axis;
   wherein the patient support assembly is configurable between:
   a first orientation, which sustains the patient in a seated position; and
   a second orientation, which sustains the patient in a generally standing position; and
   wherein the patient support assembly comprises a shin rest adjustable in position by horizontal or substantially horizontal translation, and wherein, in the second orientation, the shin rest is positioned against shins of the patient.

2. The patient positioning assembly according to claim 1, wherein, in the second orientation, the patient support assembly sustains the patient in a generally standing position such that shins of the patient are maintained at an angle relative to the vertical axis.

3. The patient positioning assembly according to claim 2, wherein the angle between the hips and the torso is between about 135° to about 165°.

4. The patient positioning assembly according to claim 1, wherein the patient support assembly includes a back rest for sustaining a back of the patient at an angle relative to the vertical axis.

5. The patient positioning assembly according to claim 4, wherein the back rest is angled posteriorly to the vertical axis at an angle between about 0° to about 20°.

6. The patient positioning assembly according to claim 4, wherein the patient support assembly is moveably mounted to the translatable member and is adapted to move in a vertical direction independently of the vertical movement of the translatable member.

7. The patient positioning assembly according to claim 1, wherein the patient support assembly includes a seat member, and wherein, in the first orientation, the seat member is positioned against buttocks of the patient for sustaining the patient in the seated position.

8. The patient positioning assembly according to claim 7, wherein the seat member is adjustable in angular orientation such that, in the second orientation, the seat member is rotated downward and is positioned posteriorly of a thigh of the patient.

9. The patient positioning assembly according to claim 1, wherein the patient support assembly includes arm rests for stabilising the patient during rotation of the patient support assembly around the vertical axis.

10. The patient positioning assembly according to claim 9, wherein the arm rests are adapted for mounting of measurement instruments thereto.

11. The patient positioning assembly according to claim 1, wherein the patient support assembly includes foot braces for securing feet of the patient.

12. The patient positioning assembly according to claim 1, wherein the patient positioning assembly further includes a base supporting the patient support assembly, the base being pivotally mounted to the translatable member such that the patient support assembly may be tilted about a point of the base.

13. The patient positioning assembly according to claim 1, wherein the patient support assembly is adapted to move in a horizontal plane.

14. The patient positioning assembly according to claim 1, wherein the radiation source is a therapeutic radiation source.

15. The patient positioning assembly according to claim 1, wherein the radiation source is a particle or photon beam.

16. The patient positioning assembly according to claim 1, wherein the therapeutic radiation source is a linear accelerator (linac) shaped by a multi-leaf collimator.

17. The patient positioning assembly according to claim 1, wherein the radiation source is a medical imaging radiation source.

18. The patient positioning assembly according to claim 17, where the medical imaging source is an MRI scanner, a positron emission tomography scanner, an ultrasound scanner, or a computed tomography scanner.

19. The patient positioning assembly of claim 1, wherein the patient support assembly further comprises a foot rest, foot brace, or foot stop.

20. A patient support assembly configurable between a first orientation, which sustains a patient in a seated position, and a second orientation, which sustains the patient in a generally standing position, wherein the patient support assembly comprises a shin rest adjustable in position by horizontal or substantially horizontal translation, and wherein, in the second orientation, the shin rest is positioned against shins of the patient.

21. The patient support assembly of claim 20, further comprising a foot rest, foot brace, or foot stop.

* * * * *